United States Patent
Mitsuhashi

(10) Patent No.: US 7,741,023 B2
(45) Date of Patent: Jun. 22, 2010

(54) METHOD FOR PREDICTING IMMUNE RESPONSE TO NEOPLASTIC DISEASE BASED ON MRNA EXPRESSION PROFILE IN NEOPLASTIC CELLS AND STIMULATED LEUKOCYTES

(75) Inventor: Masato Mitsuhashi, Irvine, CA (US)

(73) Assignees: Hitachi Chemical Co., Ltd., Tokyo (JP); Hitachi Chemical Research Center, Inc., Irvine, CA (US)

(*) Notice: Subject to any disclaimer, the term of this patent is extended or adjusted under 35 U.S.C. 154(b) by 169 days.

(21) Appl. No.: 11/917,151

(22) PCT Filed: Jun. 8, 2006

(86) PCT No.: PCT/US2006/022427

§ 371 (c)(1),
(2), (4) Date: Jan. 30, 2008

(87) PCT Pub. No.: WO2006/133399

PCT Pub. Date: Dec. 14, 2006

(65) Prior Publication Data

US 2009/0111128 A1    Apr. 30, 2009

Related U.S. Application Data

(60) Provisional application No. 60/688,744, filed on Jun. 8, 2005, provisional application No. 60/735,508, filed on Nov. 11, 2005.

(51) Int. Cl.
C12Q 1/68      (2006.01)
G01N 33/48    (2006.01)
G01N 33/574  (2006.01)

(52) U.S. Cl. .............. 435/4; 435/6; 435/7.23; 435/7.24; 436/63; 436/64

(58) Field of Classification Search ............ None
See application file for complete search history.

(56) References Cited

U.S. PATENT DOCUMENTS

| | | | |
|---|---|---|---|
| 4,880,548 A | 11/1989 | Pall et al. | |
| 4,925,572 A | 5/1990 | Pall | |
| 5,210,015 A | 5/1993 | Gelfand et al. | |
| 5,491,063 A | 2/1996 | Fisher et al. | |
| 5,683,698 A | 11/1997 | Chavali et al. | |
| 6,692,916 B2* | 2/2004 | Bevilacqua et al. | 435/6 |
| 7,332,631 B2 | 2/2008 | Hogarth et al. | |
| 2001/0006789 A1 | 7/2001 | Maino et al. | |
| 2002/0006613 A1 | 1/2002 | Shyjan et al. | |
| 2002/0048566 A1 | 4/2002 | El-Deiry et al. | |
| 2002/0106684 A1 | 8/2002 | Kopreski | |
| 2003/0138781 A1 | 7/2003 | Whitehead | |
| 2003/0148345 A1 | 8/2003 | Kopreski | |
| 2004/0265864 A1 | 12/2004 | Mitsuhashi | |
| 2007/0196835 A1 | 8/2007 | Bankaitis-Davis et al. | |
| 2008/0206761 A1 | 8/2008 | Mitsuhashi | |

| | | |
|---|---|---|
| 2008/0261207 A1 | 10/2008 | Mitsuhashi |

FOREIGN PATENT DOCUMENTS

| | | |
|---|---|---|
| EP | 1243274 A | 9/2002 |
| WO | WO 98/47004 | 10/1998 |
| WO | WO 00/76492 A1 | 12/2000 |
| WO | WO 03/040404 | 5/2003 |
| WO | WO 03/059333 A | 7/2003 |
| WO | WO 03/090694 | 11/2003 |
| WO | WO03/099312 A | 12/2003 |
| WO | WO 2005/044792 A | 5/2005 |
| WO | WO 2005/115115 | 12/2005 |
| WO | WO 2006/110091 A | 10/2006 |
| WO | WO 2006/116721 A1 | 11/2006 |
| WO | WO 2008/106451 | 9/2008 |

OTHER PUBLICATIONS

Wouters et al (Toxicology and Industrial Health, 2002, vol. 18, pp. 15-27).*

Rodriguez-Caballero et al (Laboratory Investigation, 2004, vol. 84, pp. 1387-1398).*

(Continued)

*Primary Examiner*—Karen A Canella
(74) *Attorney, Agent, or Firm*—Knobbe Martens Olson & Bear LLC

(57) ABSTRACT

Tumor necrosis factor (TNF) is capable of inducing apoptosis by interacting with specific TNF receptors on the surface of cancer cells. Because multiple members of TNF ligand and receptor are present within each superfamily, over 300 different ligand-receptor combinations exist. Activated blood leukocytes produce TNF as part of the immune response to cancer, as well as producing chemokines to attract other leukocytes to the site. A method is disclosed of detecting significant induction of a variety of TNF superfamily subtype and chemokine mRNAs in blood leukocytes when whole blood is exposed to heat-aggregated IgG or anti-T cell receptor antibodies as a model of immune system interactions. Substantial individual-to-individual variation is observed in TNF subtypes and chemokines induced. Since peripheral blood leukocytes are the supply of anti-cancer immune cells, the quantitation of ex vivo inducibility of appropriate TNF ligands and chemokines in blood will be useful in individualized cancer immunotherapy. If the tumor mass is small, such as with early invisible metastatic lesions, appropriate TNF assaults may be sufficient to prevent relapse.

13 Claims, 11 Drawing Sheets

OTHER PUBLICATIONS

Warzocha et al (Journal of Clinical Oncology, 1997, vol. 15, pp. 499-508).*

Mehmut et al (Urologia International, 2005, vol. 75, pp. 80-87).*

Schimanski, C. C., et al., "Effect of Chemokine Receptors CXCR4 and CCR7 on the Metastatic Behavior of Human Colorectal Cancer," *Clinical Cancer Research*, vol. 11, No. 5, Mar. 2005, pp. 1743-1750.

Leung, S. Y., et al., "Expression Profiling Identifies Chemokine (C-C Motif) Ligand 18 as an Independent Prognostic Indicator in Gastric Cancer," *Gastroenterology*, vol. 127, No. 2, Aug. 2004, pp. 457-469.

Moran, C. J., et al., "RANTES Expression Is a Predictor of Survival in Stage I Lung Adenocarcinoma," *Clinical Cancer Research*, vol. 8, No. 12, Dec. 2002, pp. 3803-3812.

Younes, A., et al., "Clinical Implications of the Tumor Necrosis Factor Family in Benign and Malignant Hematologic Disorders," *Cancer*, vol. 98, No. 3, Aug. 2003, pp. 458-467.

Younes, A., et al., "Emerging Applications of the Tumor Necrosis Factor Family of Ligands and Receptors in Cancer Therapy," *J. Clin. Oncol.*, vol. 21, No. 18, Sep. 2003, pp. 3526-3534.

Aggarwal, B. B., et al., "The Role of TNF and Its Family Members in Inflammation and Cancer: Lessons from Gene Deletion," *Curr. Drug Targets Inflamm. Allergy*, vol. 1, No. 4, Dec. 2002, pp. 327-341.

Sträter, J., et al., "Expression of Trail and Trail Receptors in Colon Carcinoma: Trail-R1 Is an Independent Prognostic Parameter," *Clinical Cancer Research*, vol. 8, No. 12, Dec. 2002, pp. 3734-3740.

Spierings, D. C. J., et al., "Expression of Trail and Trail Death Receptors in Stage III Non-Small Cell Lung Cancer Tumors," *Clinical Cancer Research*, vol. 9, No. 9, Aug. 2003, pp. 3397-3405.

Min, Y. J., et al., "Prognostic Significance of Fas (CD95) and Trail Receptors (DR4/DR5) Expression in Acute Myelogenous Leukemia," *Leukemia Research*, vol. 28, No. 4, Apr. 2004, pp. 359-365.

Ames et al., "Are vitamin and mineral deficiencies a major cancer risk?" Nature, 2002, 2: 694-704.

Bush et al., Cancer Chemoresistance: The relationship Between P53 and Multidrug Transporters, Int J Cancer, 2002, vol. 98, pp. 323-330.

Chaudhary et al., Prediction of response to infliximab in Crohn's disease, Digestive and Liver Disease, 2005, vol. 37, Issue 8, pp. 559-563.

Christoph Hartel et al., Delayed Cytokine mRNA Expression Kinetics after T-Lymphocyte Costimulation: A Quantitative Measure of the Efficacy of Cyclosporin A-based Immunosuppression, Clinical Chemistry, 2002, vol. 48, Issue 12, pp. 2225-2231.

Darryl See et al., Increased Tumor Necrosis Factor Alpha (TNF-α) and Natural Killer Cell (NK) Function Using an Integrative Approach in Late Stage Cancers, Immunological Investigations, 2002, vol. 31, Issue 2, pp. 137-153.

European Patent Office, EP Search Report for EP 06772657.0, Dec. 2, 2008.

Fischer et al., Melatonin reduces UV-induced reactive oxygen species in a dose-dependent manner in IL-3-stimulated leukocytes, Journal of Pineal Research, 2001, vol. 31, Issue 1, pp. 39-45.

Fukumi Sachiko et al., Differential responses of Bcl-2 family genes to etoposide in chronic myeloid leukemia K562 cells, Molecular and Cellular Biochemistry, Mar. 2000, vol. 206, Issue 1-2, pp. 43-50.

Ghosh et al., Anti-TNF therapy in Crohn's disease, Novartis Foundation Symposium, 2004, vol. 263, pp. 193-218.

Hiroko Matsunaga et al., Application of Differential Display to Identify Genes for Lung Cancer Detection in Peripheral Blood, Int. J. Cancer, 2002, vol. 100, pp. 592-599.

Hoque, et al., PUMA in Head and Neck Cancer, Cancer Letters, 2003, vol. 199, pp. 75-81.

International Search Report, International Application No. PCT/US08/83136, Jul. 17, 2009.

International Search Report, International Application No. PCT/US07/08559, Sep. 4, 2008.

International Searching Authority, International Search Report for PCT/US2005/037925, Patent Cooperation Treaty, Feb. 21, 2007.

Jamila K. Adam et al., Immune responses in cancer, Pharmacology & Therapeutics, 2003, vol. 99, pp. 113-132.

Juhasz et al., Quantification of Chemotherapeutic Target Gene mRNA Expression in Human Breast Cancer Biopsies: Comparison of Real-Time Reverse Transcription-PCR vs. Relative Quantification Reverse Transcription-PCR Utilizing DNA Sequencer Analysis of PCR Product, Journal of Clinical Laboratory Analysis, 2003, vol. 17, pp. 184-194.

Klein N. J et al., Ex-Vivo Assessment of Candidate Anti-Inflammatory Agents in the Treatment of Gram Negative Sepsis, Immunology and Infectious Diseases, 1994, vol. 4, Issue 1, pp. 33-35.

Liu Feng-Ting et al., Bax conformational change is a crucial step for PUMA-mediated apoptosis in human leukemia, Biochemical and Biophysical Research Communications, Oct. 24, 2003, vol. 310, Issue 3, pp. 956-962.

Mascheretti et al., Pharmacogenetic investigation of the TNF/TNF-receptor system in patients with chronic active Crohn's disease treated with infliximab, The Pharmacogenomics Journal, 2002, vol. 2, Issue 2, pp. 127-136.

Michael R. Verneris et al., Resistance of ex vivo expanded CD3+CD56+ T cells to Fas-mediated apoptosis, Cancer Immunol Immunother, 2000, vol. 49, pp. 335-345.

N. Gopalakrishna Iyer et al., p300 regulates p53-dependent apoptosis after DNA damage in colorectal cancer cells by modulation of PUMA/p21 levels, PNAS, May 11, 2004, vol. 101, Issue 19, pp. 7386-7391.

Plevy et al., A Role for TNF-α and Mucosal T Helper-1 Cytokines in the Pathogenesis of Crohn's Disease, The Journal of Immunology, 1997, vol. 159, Issue 12, pp. 6276-6282.

Shetty et al., Pharmacogenomics of Response to Anti-Tumor Necrosis Factor Therapy in Patients with Crohn's Disease, American Journal of Pharmacogenomics, 2002, vol. 2, Issue 4, pp. 215-221.

Spencer et al., Quantitative Analysis of Constitutive and 2,3,7,8-Tetrachlorodibenzo-p-dioxin-induced Cytochrome P450 1B1 Expression in Human Lymphocytes, Cancer Epidemiology, Biomarkers & Prevention, Feb. 1999, vol. 8, pp. 139-146.

Wen et al, TL1A-induced NF-kB Activation and c-IAP2 Production prevent DR3-mediated Apoptosis in TF-1 Cells, The Journal of Biological Chemistry, Oct. 3, 2003; 278, vol. 46, pp. 39251-39258.

Wyttenbach A et al., P53—Dependent apoptosis induced by DNA damage and its relation to ERK signalling in sympathetic neurones, Society for Neuroscience Abstract Viewer and Itinerary Planner, 2003, pp. 147.3.

Yamazaki et al., Single nucleotide polymorphisms in TNFSF15 confer susceptibility to Crohn's disease, Human Molecular Genetics, 2005, vol. 14, Issue 22, pp. 3499-3506.

* cited by examiner

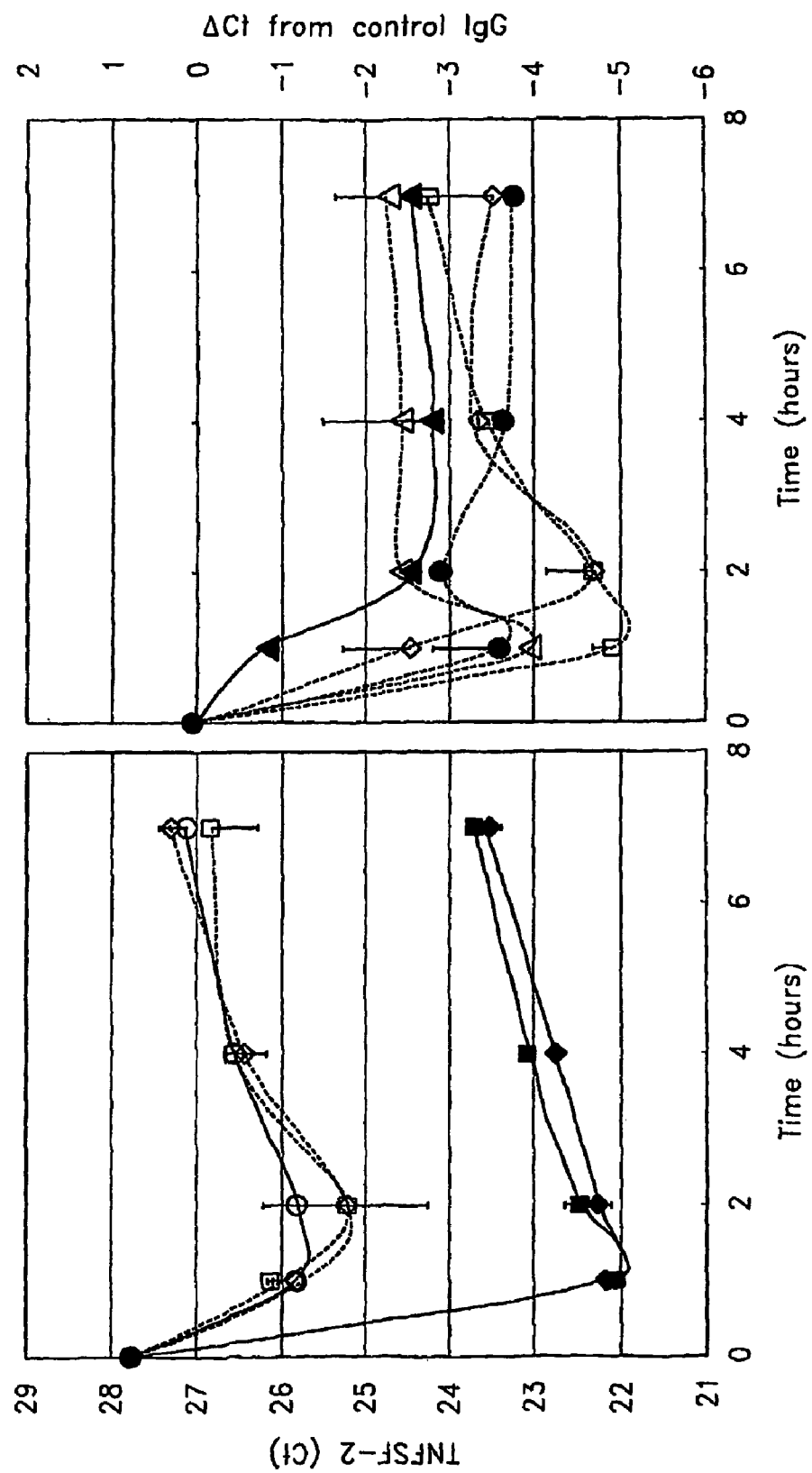

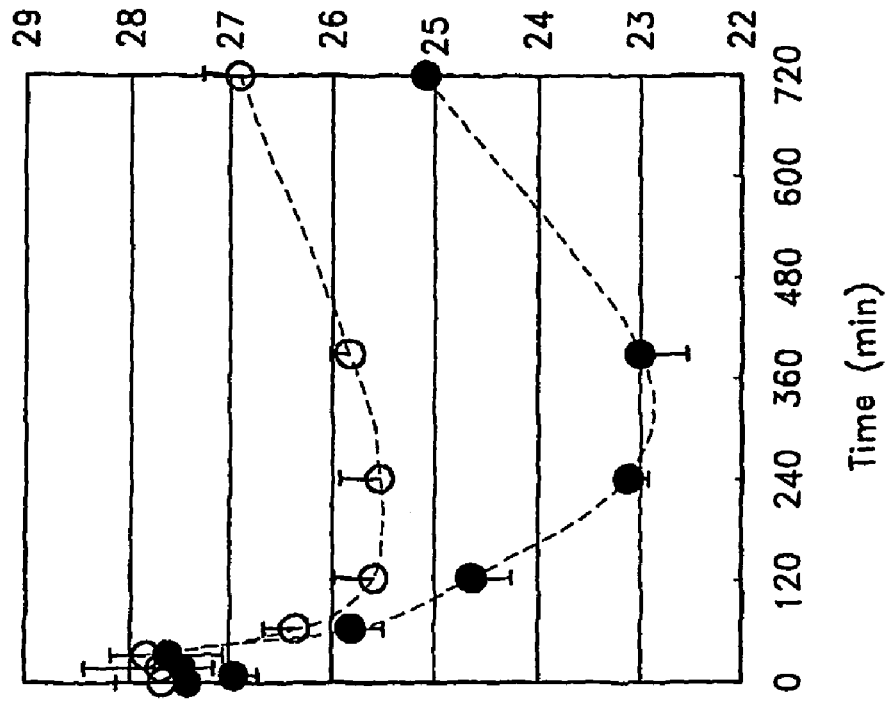
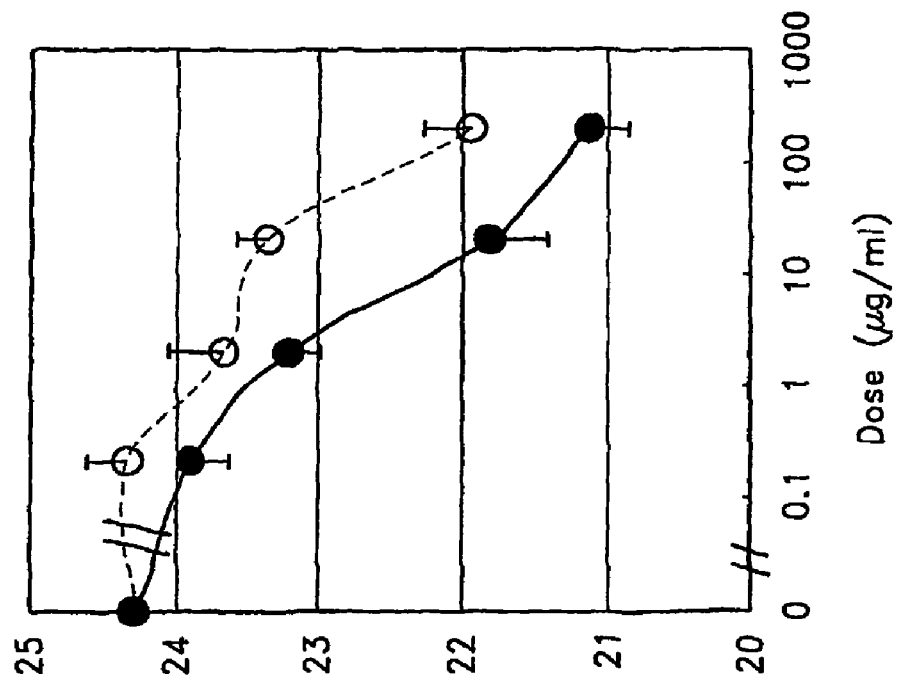
FIG. 5A
FIG. 5B

| | | |
|---|---|---|
| CCL-1 | MM282: | GGCCTGCGCCTTGGA |
| | MM283: | GGGCAGTGCCTCAGCATTT |
| CCL-2 | MM284: | CCATTGTGGCCAAGGAGATC |
| | MM285: | TGTCCAGGTGGTCCATGGA |
| CCL-3 | MM286: | CACAGAATTTCATAGCTGACTACTTTGA |
| | MM287: | TCGCTTGGTTAGGAAGATGACA |
| CCL-4 | MM288: | GGTATTCCAAACCAAAAGAAGCA |
| | MM289: | GTTCAGTTCCAGGTCATACACGTACT |
| CCL-5 | MM290: | AGTCGTCTTTGTCACCCGAAA |
| | MM291: | AGCTCATCTCCAAAGAGTTGATGTAC |
| CCL-7 | MM292: | TGTGCTGACCCCACACAGA |
| | MM293: | GCTTTGGAGTTTGGGTTTTCTTG |
| CCL-8 | MM294: | AGAGCTACACAAGAATCACCAACATC |
| | MM295: | AGACCTCCTTGCCCCGTTT |
| CCL-11 | MM296: | CCCAGAAAGCTGTGATCTTCAA |
| | MM297: | TCCTGCACCCACTTCTTCTTG |
| CCL-13 | MM298: | CCAAACTGGGCAAGGAGATCT |
| | MM299: | GGCCCAGGTGTTTCATATAATTCT |
| CCL-14 | MM300: | TGCTTCACCTACACTACCTACAAGATC |
| | MM301: | GACAATTCCGGGCTTGGA |
| CCL-15 | MM302: | CCAAGCCAGGTGTCATATTCCT |
| | MM303: | TGAGTAGGGCTTCAGCTTTTTCA |
| CCL-16 | MM304: | CAAGGATCCCAACCTACCTTTG |
| | MM305: | GGTTGACCATTCTTTGCTGTAATAATT |
| CCL-17 | MM306: | GGGCAGGGCCATCTGTTC |
| | MM307: | TCTCAAGGCTTTGCAGGTATTTAA |
| CCL-18 | MM308: | CAGATTCCACAAAAGTTCATAGTTGAC |
| | MM309: | CCGGCCTCTCTTGGTTAGG |
| CCL-19 | MM310: | CTGCTGTAGTGTTCACCACACTGA |
| | MM311: | CAGTCTCTGGATGATGCGTTCT |
| CCL-20 | MM312: | GATACACAGACCGTATTCTTCATCCTAA |
| | MM313: | TGAAAGATGATAGCATTGATGTCACA |
| CCL-21 | MM314: | CGCTCTCAGGCAGAGCTATGT |
| | MM315: | CTTGTCCAGATGCTGCATCAG |
| CCL-22 | MM316: | GCGCGTGGTGAAACACTTC |
| | MM317: | ATCGGCACAGATCTCCTTATCC |
| CCL-23 | MM318: | CGAAGCATCCCGTGTTCACT |
| | MM319: | GATGACACCCGGCTTGGA |
| CCL-24 | MM320: | CAGGAGTGATCTTCACCACCAA |
| | MM321: | GGCGTCCAGGTTCTTCATGT |
| CCL-25 | MM322: | GCGCGCCTGGACTTACC |
| | MM323: | GTAGAATATCGCAGCAGGCAGAT |
| CCL-26 | MM324: | CTGCTTCCAATACAGCCACAAG |
| | MM325: | GAGCAGCTGTTACTGGTGAATTCA |
| CCL-27 | MM326: | CGTGCTTCACCTGGCTCAA |
| | MM327: | GGTGCTCAAACCACTGTGACA |
| CCL-28 | MM328: | GGAAATGTTTGCCACAGGAAGA |
| | MM329: | TGTTTCGTGTTTCCCCTGATG |

FIG. 8A

| FIG. 8A | FIG. 8B |
|---|---|

| | | |
|---|---|---|
| CXCL-1 | MM330: | CCACTGCGCCCAAACC |
| | MM331: | GCAGGATTGAGGCAAGCTTT |
| CXCL-2 | MM332: | CCCCTGGCCACTGAACTG |
| | MM333: | TGGATGTTCTTGAGGTGAATTCC |
| CXCL-3 | MM334: | GGAATTCACCTCAAGAACATCCA |
| | MM335: | GTGGCTATGACTTCGGTTTGG |
| CXCL-4 | MM336: | CCGTCCCAGGCACATCAC |
| | MM337: | GCAAATTTTCCTTCCATTCTTCA |
| CXCL-5 | MM338: | AGAGCTGCGTTGCGTTTGT |
| | MM339: | TGGCGAACACTTGCAGATTACT |
| CXCL-6 | MM340: | CAGAGCTGCGTTGCACTTGT |
| | MM341: | ACACCTGCAGTTTACCAATCGTT |
| CXCL-7 | MM342: | TCTGGAATTCATCCCAAAAACA |
| | MM343: | ACTTCGACTTGGTTGCAATGG |
| CXCL-9 | MM344: | CCACCTACAATCCTTGAAAGACCTT |
| | MM345: | CAGTGTAGCAATGATTTCAATTTTCTC |
| CXCL-10 | MM346: | TCCACGTGTTGAGATCATTGC |
| | MM347: | TCTTGATGGCCTTCGATTCTG |
| CXCL-11 | MM348: | AGGACGCTGTCTTTGCATAGG |
| | MM349: | GCATCGTTGTCCTTTATTTTCTTTC |
| CXCL-12 | MM350: | TGCCAGAGCCAACGTCAAG |
| | MM351: | CAGCCGGGCTACAATCTGA |
| CXCL-13 | MM352: | GACGCTTCATTGATCGAATTCA |
| | MM353: | TTCTTCCAGACTATGATTTCTTTTCTTG |
| CXCL-14 | MM354: | AAGCTGGAAATGAAGCCAAAGT |
| | MM355: | ACACGCTCTTGGTGGTGATG |
| CXCL-16 | MM356: | CCCACAGCCAGGACATCAG |
| | MM357: | CTTGCACAGCACATAGGAAAGG |
| IL-8 | MM358: | TGCTAAAGAACTTAGATGTCAGTGCAT |
| | MM359: | TGGTCCACTCTCAATCACTCTCA |
| IL-5 | MM360: | GCTCTTGGAGCTGCCTACGT |
| | MM361: | AAGGTCTCTTTCACCAATGCACTT |
| IL-6 | MM362: | TCATCACTGGTCTTTTGGAGTTTG |
| | MM363: | TCTGCACAGCTCTGGCTTGT |
| IL-12A | MM364: | GCAGGCCCTGAATTTCAACA |
| | MM365: | GAAGTATGCAGAGCTTGATTTTAGTTTTA |
| IL-12B | MM366: | CGGTCATCTGCCGCAAA |
| | MM367: | CCCATTCGCT CCAAGATGAG |
| IL-15 | MM368: | TGAAGTGCTTTCTCTTGGAGTTACA |
| | MM369: | CATTCCCATTAGAAGACAAACTGTTG |
| IL-16c | MM370: | AAAACCTCTTGGGAAGCATGAG |
| | MM371: | GGGACCCCGAGGACAGTACT |
| IL-1B | MM372: | GAAGATGGAAAAGCGATTTGTCTT |
| | MM373: | GGGCATGTTTTCTGCTTGAGA |

METHOD FOR PREDICTING IMMUNE RESPONSE TO NEOPLASTIC DISEASE BASED ON MRNA EXPRESSION PROFILE IN NEOPLASTIC CELLS AND STIMULATED LEUKOCYTES

RELATED APPLICATIONS

This application claims priority to U.S. Provisional Application Nos. 60/688,744 filed on Jun. 8, 2005 and 60/735,508 filed on Nov. 11, 2005.

BACKGROUND OF THE INVENTION

1. Field of the Invention

The present invention relates to a method for predicting the immune response in a mammal to neoplastic disease based on the expression profile of tumor necrosis factor receptor (TNF-R) superfamily mRNA in neoplastic tissue, and of tumor necrosis factor (TNF) superfamily mRNA in circulating leukocytes. In the method, samples of neoplastic tissue are obtained and the TNF-R superfamily subtype mRNAs expressed in those tissues are assessed. Furthermore, whole blood of the mammal is subjected to a stimulus that activates T-cells in the blood and the TNF superfamily subtype mRNAs that exhibit a significant change in expression level in response to the stimulus are identified. Individuals that exhibit a change in expression level in TNF superfamily subtypes that correlate with the TNF-R superfamily subtypes expressed in their tumor tissue are determined to have a likely lesser severity of prognosis for their disease.

2. Description of the Related Art

Different modalities of cancer therapies may be compared to varying types of uses of force in society. Chemotherapy is like the widespread use of military force in a city; the overwhelming power of the weapons involved may cause collateral damage to civilians. In contrast, leukocytes in circulating peripheral blood, which are the primary killers of cancer cells in the human body, are like police officers patrolling city streets who deal with street crime. Likewise, when leukocytes encounter cancer cells in the body, these cells are the initial responders to the cancer targets. Leukocytes are classified into many classes and subclasses based on morphological analysis and characterization of cell surface markers using flow cytometry or immunohistochemical staining techniques. These classes and subclasses are like identifying police officers by their uniforms and identification budges. The number of leukocytes per $mm^3$ of peripheral blood corresponds to the number of officers in the city.

When a police officer encounters street criminals, he must deal with them with the weapons he has at hand. But police officers are not always carrying appropriate weaponry. Similarly, cytotoxic T-cells are not always provided with the proper anti-tumor factors to combat specific cancer cells. Cytotoxic T-cells recognize cancer cells via IgG Fc receptors (FcγR), when the cancer cells are coated with IgG. This process is termed antibody-dependent cell-medicated cytotoxicity (ADCC). In fact, IgG is frequently recognized around cancer margins by staining with anti-human IgG (see, for example, Richman A V, *Immunofluorescence studies of benign and malignant human mammary tissue*, J. Natl. Cancer Inst. 1976; 57:263-7, and Koneval T, et al., Demonstration of immunoglobulin in tumor and marginal tissues of squamous cell carcinomas of the head and neck, J. Natl. Cancer Inst. 1977; 59:1089-97). Infiltration of mononuclear leukocytes into cancer lesions is also found in many cases. The FcγR on the surface of cytotoxic T-cells are like a bag containing an assortment of weapons that a police officer carries. Different types of FcγR, such as CD16, CD32, and CD64 correspond to different types of bags. Cudgels are an initial weapon, and are held ready to attack at any time. In cytotoxic T-cells, the cudgel corresponds to perforin (see Nakanishi et al., *Perforin expression in lymphocytes infiltrated to human colorectal cancer*, Br. J. Cancer 1991; 64:239-42), which is pre-synthesized and stored in the cytosol of cytotoxic T-cells, and immediately released upon FcγR activation. Other presynthesized "cudgels" ready for use include granzymes, proteases related to the digestive enzymes trypsin and chymotrypsin, which may act to trigger apoptosis in the target cell.

Officers also carry more powerful guns, which may correspond to tumor necrosis factors (TNF) in cytotoxic T-cells. Usually, the "bullets" in the cellular context (TNF subtypes) are not loaded in the gun, and are synthesized and released from cytotoxic T-cells only upon Fc receptor activation. TNF is capable of inducing apoptosis by interacting with specific TNF receptors present on the surface of target cells. In order to maintain killing activities against a broad spectrum of target cells, different types of TNF ligands exist (as part of a TNF superfamily, abbreviated to TNFSF). According to GenBank and UniGene information (http://www.ncbi.nlm.nih.gov), the human TNF superfamily encompasses up to TNF superfamily 18, with some missing numbers (16 and 17) and multiple sequences within the same number (13A and 13B), for a total of 17 human members. For the corresponding TNF receptors (the TNF-R superfamily: abbreviated to TNFRSF), the human TNF-R superfamily encompasses up to TNF-R superfamily subtype 21. Although TNF/TNF-R superfamily subtype interactions are not strictly specific, each ligand generally reacts with a specific receptor, as shown in Table 1, and over 300 different TNF superfamily subtype TNF-R superfamily combinations exist.

TABLE I

List of GenBank UniGene entry of TNFRSF and TNFSF mRNA.

| TNFRSF (UniGene #) | Corresponding TNFSF (UniGene #) |
|---|---|
| 1A (Hs.279594) | 2 (Hs.241570) |
| 1B (Hs.256278) | 2 (Hs.241570) |
| 3 (Hs.1116) | 1 (Hs.36) |
|  | 3 (Hs.376208) |
| 4 (Hs.129780) | 4 (Hs.181097) |
| 5 (Hs.472860) | 5 (Hs.652) |
| 6 (Hs.244139) | 6 (Hs.2007) |
| 7 (Hs.355307) | 7 (Hs.501497) |
| 8 (Hs.1314) | 8 (Hs.494901) |
| 9 (Hs.193418) | 9 (Hs.1524) |
| 10A (Hs.401745) | 10 (Hs.478275) |
| 10B (Hs.521456) | 10 (Hs.478275) |
| 10C (Hs.119684) | 10 (Hs.478275) |
| 10C (Hs.119684) | 10 (Hs.478275) |
| 10D (Hs.213467) | 10 (Hs.478275) |
| 11A (Hs.204044) | 11 (Hs.333791) |
| 11B (Hs.81791) | 11 (Hs.333791) |
| 12A (Hs.355899) | 12 (NM003809)* |
| 14 (Hs.512898) | 14 (Hs.129708) |
| 17 (Hs.2556) | 13 (Hs.54673) |
|  | 13B (Hs.525157) |
| 18 (Hs.212680) | 18 (Hs.248197) |
| 25 (Hs.462529) | 15 (Hs.241382) |

*GenBank accession number (no UniGene entry was found).

The complete eradication of cancers may happen when the appropriate TNF superfamily subtype is released from infiltrating cytotoxic T-cells. The rare cases of miracle survivors of cancers may be those in which the TNF superfamily subtype TNF-R superfamily subtype combination is perfect.

Antibody-dependent cell-mediated cytotoxicity (ADCC) is another mechanism involved in the cytolytic function of leukocytes in conjunction with antibodies (see Perussia et al., *Assays for antibody-dependent cell-mediated cytotoxicity (ADCC) and reverse ADCC (redirected cytotoxicity) in human natural killer cells*, Methods Mol. Biol. 2000; 121: 179-92). Once the Fab portion of IgG binds to the target cells, the Fc portion of IgG activates Fc receptors on the leukocytes, followed by activation of these leukocytes to attack target cells. Although ADCC has been studied for many years, the conditions in in vitro experiments involving ADCC is dependent on the ratio between effector cytotoxic T-cells and target cells in a pure cell system suspended in an artificial solution. Moreover, because cytolysis was generally quantitated by the release of isotope (chromium-51) from the target cells, it was not known whether the observed cytolysis happens via perforin or TNF. It is also not known which TNF superfamily subtypes are involved in ADCC.

Finally, a further important mechanism by which leukocytes combat cancer is the release of chemokines to recruit more leukocytes to the disease site. Many such cytokines have been discovered. Although correlations have not been established between specific chemokines and specific populations of recruited leukocytes, the phenomenon of chemokine release and leukocyte recruitment is important in combating cancer. An analogy might be made here to policemen confronted with a gang of criminals, who radio back to headquarters for more reinforcements.

In sum, although complicated cellular mechanisms are required to educate appropriate subsets of leukocytes to be able to recognize specific cancer markers, and appropriate chemotactic factors should be released to attract these mature leukocytes to the lesion, actual cancer killing happens in two distinct ways. Immediate cancer killing takes place by the release of perforin from these leukocytes, followed by slow and sustained induction of apoptosis via the synthesis and release of TNF (see Vujanovic, *Role of TNF family ligands in antitumor activity of natural killer cells*, Int. Rev. Immunol. 2001 June; 20(3-4):415-37). TNF induces apoptosis via binding to the specific receptors on the target cell surface. This means that leukocytes must release specific TNF ligand(s) corresponding to the receptors present on the cancer cells. Although the usefulness of TNF/TNF receptor ratios as predictors of disease outcome has been considered (see McDermott, *TNF and TNFR biology in health and disease*, Cell. Mol. Biol. (Noisy-le-grand). 2001 June; 47(4):619-35), little is known about the profile of TNF receptors in cancer cells and induction of ligands in leukocytes, nor is it known how appropriate populations of leukocytes are recruited.

SUMMARY OF THE INVENTION

If a pathological specimen shows IgG deposition around cancer margins, this means that the patient is at least capable of raising cancer-recognizing IgG. If the infiltration of mononuclear leukocytes exists at the margin of the cancer mass, this means that the patient's leukocytes are somehow attracted toward the cancer lesion, probably due to the release of chemotactic factors (C3a, C5a, C567) (see Becker, *The relationship of the chemotactic behavior of the complement-derived factors, C3a, C5a, and C567, and a bacterial chemotactic factor to their ability to activate the proesterase 1 of rabbit polymorphonuclear leukocytes*, J. Exp. Med. 1972; 135:376-87) during complement activation of cancer-bound IgG. The type of TNF-R superfamily subtypes expressed on the surface of cancer cells can be identified by, for example, immunostaining (if antibodies are available), in-situ hybridization, or in-situ PCR (sequences are available from GenBank). Identification of the TNF superfamily subtypes expressed in infiltrating mononuclear cells is difficult to interpret, because FcγR may not be activated yet. Since leukocytes in peripheral blood are like reserve police officers, a supply of appropriately and fully equipped cytotoxic T-cells in peripheral blood is a critical first step for the battle against cancer. Thus, this method makes it possible to predict anti-cancer immunity in each patient by quantitating the inducibility of the appropriate TNF superfamily subtypes in peripheral blood leukocytes.

Accordingly, an embodiment of the present invention provides a method of determining the likely severity of prognosis for a neoplastic disease in a mammal, comprising: determining a level of expression of a plurality of tumor necrosis factor (TNF) superfamily subtypes in a first sample of whole blood from the mammal; exposing a second sample of whole blood of the mammal to a stimulus that activates leukocytes in the whole blood; determining a level of expression of the plurality of tumor necrosis factor (TNF) superfamily subtypes in the second sample; identifying subtypes that exhibit a significant change in expression level in said whole blood between the first and second samples; and determining a likely lesser severity of prognosis when the identified subtypes of TNF superfamily correspond to specific tumor necrosis factor receptor (TNF-R) superfamily subtypes expressed in neoplastic cells of the mammal.

In a further aspect, the TNF-R superfamily subtypes expressed in the neoplastic tissue are selected from the group consisting of TNF-R superfamily subtypes 1A, 3, 12A, and 14. In another aspect, the TNF-R superfamily subtypes expressed in the neoplastic tissue are identified. In a further aspect, the TNF-R superfamily subtypes expressed in the neoplastic tissue are identified by a method selected from the group consisting of immunostaining, in situ hybridization, in situ polymerase chain reaction, and in vitro polymerase chain reaction.

In a further aspect, exposing whole blood includes addition of heparin. In another aspect, the stimulus is selected from the group consisting of heat-aggregated human IgG and anti-human α/β T-cell receptor monoclonal IgG. In a further aspect, the tumor necrosis factor receptor superfamily subtypes expressed by diseased cells are selected from the group consisting of TNF-R superfamily subtypes 1A, 1B, 3, 4, 5, 6, 7, 8, 9, 10A, 10B, 1C, 10D, 11A, 11B, 12A, 14, 17, 18, and 25. In another aspect, the tumor necrosis factor superfamily mRNA subtypes expressed in said exposed whole blood are selected from the group consisting of TNF superfamily subtypes 1, 2, 3, 4, 5, 6, 7, 8, 9, 10, 11, 12, 13, 13B, 14, 15, and 18.

Another embodiment provides a method of determining the likely severity of prognosis for a neoplastic disease in a mammal, comprising: determining a level of expression of a plurality of chemokines in a first sample of whole blood from the mammal; exposing a second sample of whole blood of the mammal to a stimulus that activates leukocytes in the whole blood; determining a level of expression of the plurality of chemokines in the second sample; and determining a likely lesser severity of prognosis when chemokines that exhibit a significant change in expression level in the whole blood between said first and second samples are identified. In a further aspect, the chemokines are selected from the group consisting of CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL9, CXCL10, CXCL11, CXCL12, CXCL13, CXCL14, CXCL16, IL1B, IL5, IL6, IL8, IL12A, IL12B, IL15, and IL16.

A further embodiment of the invention provides a method of determining the likely utility of a dietary component for treating neoplastic disease in a mammal, comprising: obtaining a first sample of whole blood of the mammal; exposing a second sample of whole blood of the mammal to the dietary component; exposing the first and second samples of whole blood of the mammal to a stimulus that activates leukocytes in the whole blood; determining a level of expression of a plurality of tumor necrosis factor (TNF) superfamily subtypes in the first and second samples of whole blood from the mammal; identifying subtypes that exhibit a significant change in expression level in said whole blood between said first and second samples; and determining that the dietary component likely has utility for treating the neoplastic disease when the identified subtypes of TNF superfamily correspond to specific TNF-R superfamily subtypes expressed in neoplastic cells of the mammal.

In a further aspect, the first sample is exposed to a control stimulus before the exposure to the stimulus that activates leukocytes in the whole blood. In another aspect, TNF-R superfamily subtypes expressed in neoplastic tissue are selected from the group consisting of TNF-R superfamily subtypes 1A, 3, 12A, and 14. In a further aspect, TNF-R superfamily subtypes expressed in the neoplastic tissue are identified. In another aspect, TNF-R superfamily subtypes expressed in neoplastic tissue are identified by a method selected from the group consisting of immunostaining, in situ hybridization, in situ polymerase chain reaction, and in vitro polymerase chain reaction.

BRIEF DESCRIPTION OF THE DRAWINGS

FIG. 4A shows the results of an analysis of the dose response and kinetics when peripheral blood leukocytes are exposed to anti-TCR antibody and TNF superfamily subtype 2 mRNA expression is quantified.

FIG. 4B shows the results of an analysis of the kinetics when peripheral blood leukocytes are exposed to anti-TCR antibody and TNF superfamily subtype 2 mRNA expression is quantified.

FIG. 5A shows the results of an analysis of the dose response and kinetics when peripheral blood leukocytes are exposed to HAG and TNF superfamily subtype 15 mRNA expression is quantified.

FIG. 5B shows the results of an analysis of the kinetics when peripheral blood leukocytes are exposed to HAG and TNF superfamily subtype 15 mRNA expression is quantified.

FIG. 8 shows the chemokine primer sequences employed in Embodiment 4.

DETAILED DESCRIPTION OF THE PREFERRED EMBODIMENT

Quantitation of mRNA

Figures 1A, 1B:
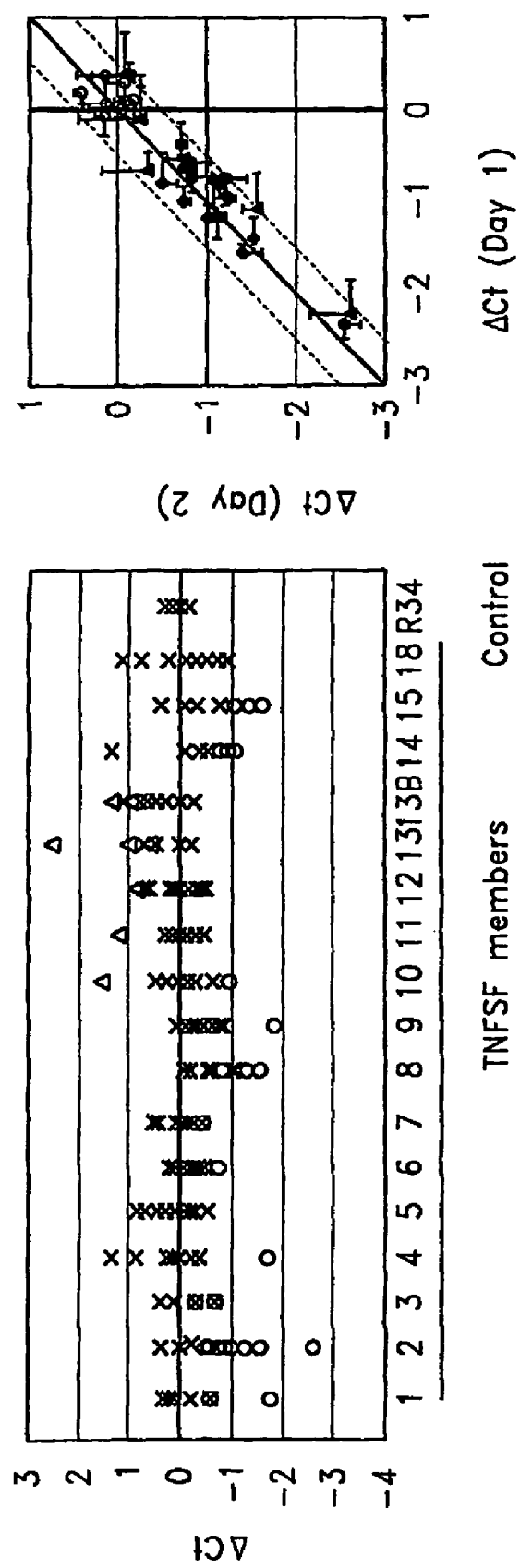
FIG. 1A shows the results of an analysis of TNF superfamily mRNAs induced in peripheral blood leukocytes after exposure of whole blood to heat-aggregated IgG (HAG).
FIG. 1B shows the results of a repetition of the analysis of FIG. 1A.

The present inventors have developed a unique technology known as the Hem(A)$^+$ system that is capable of quantitating minute changes of gene expression in whole blood leukocytes. This technology is described in detail in U.S. patent application Ser. No. 10/796,298, and International Patent Application Serial No. PCT/US2004/036309, both incorporated here by reference (see also Mitsuhashi, *Absolute quantitation of mRNA in human blood leukocytes as a model for phenotypic gene expression-based diagnostics*, Clin Chem, 52:4 (2006)).

In the quantitation technique, whole blood is applied to 96-well filterplates to trap leukocytes. Lysis buffer containing both synthetic external control RNA and specific reverse primers is added to the filterplates, and cell lysates are transferred to oligo(dT)-immobilized microplates for hybridization. The cDNA is then synthesized in the oligo(dT)-immobilized microplates from these primer sites. The solution, which contains specific reverse primer-primed cDNA, is used for real-time PCR. The plate containing oligo(dT)-primed immobilized cDNA may be stored as a cDNA bank.

In more detail, the assay procedure consists of 3 major steps: (a) leukocyte isolation and lysis on filterplates; (b) mRNA isolation, reverse primer hybridization, and cDNA synthesis in oligo(dT)-immobilized microplates; and (c) real-time quantitative PCR. Custom 96-well filterplates may be manufactured, for example by Whatman or Pall, by assembly with leukocyte reduction membranes (Leukosorb; Pall). These filterplates are placed over collection plates, and 150 ΔL of 5 mmol/L Tris (pH 7.4) is applied to wet the filter membranes. After centrifugation at 120 g for 1 min at 4° C. to remove the Tris solution from the membranes, 50 μL of well-mixed whole blood sample is applied to each well and immediately centrifuged at 120 g for 2 min at 4° C. The wells are then washed once with 300 μL of phosphate-buffered saline. After centrifugation at 2000 g for 5 min at 4° C. to remove the saline solution, 60 μL of stock lysis buffer [5 g/L N-lauroyl-sarcosine, 4× standard saline citrate, 10 mmol/L Tris-HCl (pH 7.4), 1 mmol/L EDTA, 1 mL/L IGEPAL CA-630 (substitute of NP-40), 1.79 mol/L guanidine thiocyanate (all from Sigma)], supplemented with 1 mL/L 2-mercaptoethanol (Bio-Rad), 0.5 g/L proteinase K (Pierce), 0.1 g/L salmon sperm DNA (5 Prime Eppendorf/Brinkman), 0.1 g/L *Escherichia coli* tRNA (Sigma), 5 nmol/L each of the specific reverse primers, and $10^9$ molecules/L of synthetic RNA34 (as external control), are added to each well of the filterplates. The plates are then incubated at 37° C. for 10 min, placed over oligo(dT)-immobilized microplates (GenePlate; RNAture), and centrifuged at 2000 g for 5 min at 4° C. After overnight storage at 4° C., the microplates are washed 3 times with 100 µL of plain lysis buffer and then 3 times with 150 mL of wash buffer [0.5 mol/L NaCl, 10 mmol/L Tris (pH 7.4) 1 mmol/L EDTA] at 4° C.

cDNA can be synthesized directly in each well by addition of 30 mL of buffer containing 1× reverse transcription buffer [50 mM KCl, 10 mM Tris-HCl (pH 8.3), 5.5 mM $MgCl_2$, 1 mL/L Tween 20], 1.25 mM of each deoxynucleoside triphosphate, 4 units of rRNasin, and 80 U of MMLV reverse transcriptase (Promega; without primers) and incubation at 37° C. for 2 h. From each 30-µL reaction, 4 µL of cDNA is transferred directly to 384-well PCR plates, and 5 mL of TaqMan universal master mixture (Applied Biosystems) and 1 µL of oligonucleotide cocktail (5 µM each of the forward and reverse primers, and 1—2 µM TaqMan probe) are added. PCR may be carried out in a PRISM 7900HT (Applied Biosystems), with 1 cycle of 95° C. for 10 min followed by 45 cycles of 95° C. for 30 s, 55° C. for 30 s, and 60° C. for 1 min. Each gene is amplified in separate wells. The cycle threshold (Ct), i.e., the cycle at which certain amounts of PCR products (based on fluorescence) are generated, is determined with analytical software (SDS; Applied Biosystems).

To construct calibration curves for quantification, long synthetic DNA oligonucleotides containing sequences of the forward and reverse primers and TaqMan probes are synthesized for each target. The TaqMan probe for control RNA34, for example, is CCAAGGCCCAGCCCTCACACA. Alternatively, SYBRGreen PCR may be employed. Each oligonucleotide may be purified by HPLC to a purity of >95%. Each PCR contains $10-10^6$ molecules/well of these template oligonucleotides. The calibration curve for control RNA34 generated by DNA oligonucleotides may be used to convert the Ct values of the samples to molecules/PCR well (4 µL of cDNA), which are then multiplied by 7.5 (30 divided by 4) to obtain molecules/sample (30 µL of cDNA). The percentage recovery of RNA34 is obtained by dividing these values by the amounts of RNA34 in the original 60 µL of lysis buffer ($6 \times 10^5 = 10^7$/mL×60 mL). For native mRNA, the molecules/PCR well are determined as described above with the respective calibration curves, and then these values are converted to molecules per microliter of blood by multiplying by 7.5 (30 divided by 4), dividing by the percentage recovery of RNA34 in each sample, and dividing by the volume of blood added to each well of the filterplates (usually 50 µL). The mean (SD) is calculated from triplicate aliquots of whole blood and the Student t-test may be used for statistical analyses.

In embodiments, the expression profile of TNF receptor superfamily (TNFRSF) mRNA was characterized among various cancer specimens by using the mRNA quantitation system (Hem(A)$^+$) described above. Then the inducibility of TNF superfamily (TNFSF) mRNA was quantitated by stimulating heparinized whole blood with mouse anti-human T cell receptor monoclonal antibody or heat-aggregated IgG as ex vivo models of cytotoxic T-cell mediated reaction and antibody dependent cell cytotoxicity (ADCC), respectively. Significant induction or reduction in the expression levels was calculated using statistical methods well known in the art; a p value of 0.05 or less was employed. The substantial individual-to-individual variation shown indicates that embodiments of the present invention may be employed in laying the groundwork for individualized cancer immunotherapy.

Embodiment 1

The mRNA quantitation method described above was employed to quantitate all types of TNF superfamily mRNA, both with and without ex vivo stimulation using heat-aggregated IgG (HAG), which was employed as a model of immune complex stimulation (see Ostreiko et al., *Production and characterization of heat-aggregated IgG complexes with pre-determined molecular masses: light-scattering study*, Immunol Lett. 1987; 15:311-6). The immune complex is formed when IgG molecules bound to a target cell bind with high avidity to Fc receptors on a leukocyte, causing cross-linking of the Fc receptors and generation of a leukocyte activation signal.

Triplicate aliquots of 50 µL each of heparinized whole blood was incubated with 200 µg/mL HAG at 37° C. for 2 hours. Then blood samples were applied to 96-well filterplates to trap leukocytes, and cell lysates were transferred to 96-well oligo(dT)-immobilized microplates for isolation of poly(A)$^+$ mRNA as described above. cDNA was synthesized on the microplates and was used for real-time polymerase chain reaction (PCR) in 384-well plates by monitoring SYBR Green fluorescence (see Morrison et al., *Quantification of low-copy transcripts by continuous SYBR Green I monitoring during amplification*. Biotechniques 1998; 24:954-8, 960, 96). In brief, SYBR Green PCR was conducted by diluting cDNA 3-4 fold in water, and transferring 4 µl cDNA solution directly to 384-well PCR plates, to which 5 µl of a master mix (BioRad, Hercules, Calif.) and 1 µl of oligonucleotide cocktail (15 µM each of forward and reverse primer) were applied, and conducting PCR in PRISM 7900HT (ABI), with one cycle of 95° C. for 10 min followed by 45 cycles of 95° C. for 30 sec and 60° C. for 1 min. Each gene was amplified in separate wells. The Ct was determined by analytical software (SDS, ABI). The PCR conditions were carefully optimized, so that a single appropriate peak was detected on melting curve analysis without any primer dimers. To validate the assay conditions, synthetic RNA34 was spiked into the lysis buffer, and this RNA34 was also quantitated by real time PCR. The sequence specificity of primers was confirmed by blast analysis (http://www.ncbi.nlm.nih.gov/BLAST). The Ct was set equal to the PCR cycle where certain amounts of PCR products were generated, and delta Ct (ΔCt) was also calculated by subtracting the Ct values of the un-stimulated samples from those of the stimulated samples. Since Ct is a log scale, 1 ΔCt means double or one half in quantity, and a negative ΔCt indicates an increase in expression.

The results are shown in FIGS. 1A and 1B. In the Figures, TNFSF mRNAs (1-18) and spiked control RNA34 were quantitated by SYBR Green real time PCR. ΔCt values of 3, 2, 1, 0, −1, −2, and −3 indicate ⅛, ¼, ½, 0, 2, 4, 8 fold increases, respectively. In FIG. 1A, each symbol is the mean value from each individual. The ○ symbol indicates a significant increase (p<0.05), while the Δ symbol indicates a significant decrease (p<0.05), and X indicates no change. FIG. 1B shows the results of repeating the analysis twice in 2 consecutive days using the same individuals. The symbols are the mean±standard deviation from each individual. ●: TNFSF-2 (TNFα), ▲: TNFSF-8, ♦: TNFSF-15, respectively. The solid line is the line where two data sets are identical. The dotted lines indicate ±0.5 ΔCt.

This technique was capable of detecting basal levels of all members of TNF superfamily mRNA in blood leukocytes. As shown in FIG. 1A, significant induction of TNF superfamily mRNA was identified when whole blood was exposed to HAG. Although large individual-to-individual variation exists, the dominant TNF superfamily mRNAs were TNF superfamily subtypes 2 (TNFα), 8, and 15. These mRNAs exhibited a HAG-induced response in, respectively, 80% (¹²⁄₁₅), 73% (¹¹⁄₁₅), and 60% (⁹⁄₁₅) of the tested individuals. TNF superfamily subtypes 1, 3, 4, 6 (i.e., FasL), 7, 9, 10 (i.e., TRAIL), 14, and 18 mRNAs exhibited a HAG-induced response in at least one tested individual. TNF superfamily subtypes 5, 11, 12, 13, and 13B mRNAs exhibited no HAG-induced response in any of the tested individuals. At least one of TNF superfamily subtypes 2, 8 and 15 was induced by HAG exposure in every tested individual. For example, three individuals that exhibited no HAG-induced TNF superfamily subtype 2 response all exhibited a subtype 15 response, whereas six individuals that exhibited no HAG-induced subtype 15 response exhibited a subtype 2 response. Four individuals in which TNF superfamily subtype 8 exhibited no HAG-induced response did exhibit a response in either subtype 2 or subtype 15. The ΔCt of the control, spiked RNA34, was all within ±0.5, as shown in FIG. 1A. In order to further validate these experiments, blood samples were obtained from the same individuals twice in 2 consecutive days. As shown in FIG. 1B, the values for TNF superfamily subtypes 2, 8, 15 and RNA34 were reproducible within ±0.5 standard deviation. The variation within triplicate whole blood aliquots in each sample was also less than 0.5 ΔCt (FIG. 1B, X-Y bar in each symbol).

This method may be applied in the following manner in an embodiment. Specimens of cancers removed from mammalian patients undergoing surgical removal or biopsy are analyzed for IgG deposition, infiltration of mononuclear leukocytes, and the type of TNF-R superfamily subtypes expressed on cancer cells. Blood samples are then obtained from the same individuals, and subjected to analysis to determine which types of TNF superfamily mRNA are induced by HAG stimulation and to what degree. Individuals are classified into a group in which the induced TNF superfamily and the expressed TNF-R match and a group in which they do not match. The results of a comparison of clinical outcomes in the 2 groups will reveal that the matching group exhibits a lesser severity of prognosis. If the cancer mass is small, such as with early invisible metastatic lesions, appropriate TNF superfamily-mediated immune system attack may be sufficient to prevent cancer relapse. The clinical outcomes compared should thus include the length of remission, and frequency of relapse (metastasis).

Embodiment 2

DNA sequences of TNF-R superfamily and TNF superfamily mRNA were downloaded from GenBank, as shown in Table 1, and the primer sequences shown in Table 2 below were designed by Primer Express (Applied Biosystems) and HYBsimulator (RNAture). These sequences were designed at common regions among multiple transcripts if such variants exist. No amplification happened without cDNA (no primer dimer), and a single peak was detected at melting curve analysis.

TABLE 2

Primer sequences used

| Target mRNA | Forward | Reverse |
| --- | --- | --- |
| TNFRSF-1A | CCTGCCAGGAGAAACAGAACA | GGAGACACACTCGTTTTCTCTTAGAA |
| TNFRSF-1B | CAAGCCAGCTCCACAATGG | TGACCGAAAGGCACATTCCT |
| TNFRSF-3 | CCTCCCGGGCTCTCTACAC | TCATGGGTGATAAATTGGTTCCT |
| TNFRSF-4 | ACGACGTGGTCAGCTCCAA | GCGGCAGACTGTGTCCTGTGT |
| TNFRSF-5 | GGCCAAGAAGCCAACCAATA | GAAGATCGTCGGGAAAATTGAT |
| TNFRSF-6 | TGGCATCAACTTCATGGAAAGA | GCAAGAGTACAAAGATTGGCTTTTT |
| TNFRSF-7 | CTGCAGAGCCTTGTCGTTACAG | GCTCCGGTTTTCGGTAATCC |
| TNFRSF-8 | GGTTGAGGCAGCAAACAGATG | GCCTGGTGGTTAAGGTCTGATG |
| TNFRSF-9 | CGTCGACTGCGTTGCTCTT | TTCTGCCCCGTTAACAACAG |
| TNFRSF-10A | TGAGGACAATGCTCACAACGA | TTGCTGCTCAGAGACGAAAGTC |
| TNFRSF-10B | CTGAGACAGTGCTTCGATGACTTT | CCATGAGGCCCAACTTCCT |
| TNFRSF-10C | GGAAGTGTAGCAGGTGCCCTAGT | ACCAAATTCTTCAACACACTGGATAT |
| TNFRSF-10D | ATGGACTTACGAGGGTTCGACTTAG | GGAAAAGAGATGTACAGCCTACAGTAGTAAGC |
| TNFRSF-11A | GGAAACAGTAACTCCACGTTCATCT | GCGAGGTCTGGCTGACGTA |
| TNFRSF-11B | TGCAAACCCAGTGACCAGATC | AAGGTGTCTTGGTCGCCATT |
| TNFRSF-12A | CGCTGATCCAGTGACAATGTG | GCGTCTGGGAGGCAGAGA |
| TNFRSF-14 | CAGGGAGCCTCGTCATCGT | CACCCCTTGGCTTTCTTCTTT |
| TNFRSF-17 | GGAGGAAGGCGCAACCAT | GCAGCTGGCAGGCTCTTG |
| TNFRSF-18 | AGTTTTGGCTTCCAGTGTATCGA | GCAGTCTGTCCAAGGTTTGCA |
| TNFRSF-25 | CCTGCTCGCCCCTATCG | TTCACCCCCTCTCGACATTC |
| TNFSF-1 | CAGCTATCCACCCACACAGATG | CGAAGGCTCCAAAGAAGACAGT |

TABLE 2-continued

Primer sequences used

| Target mRNA | Forward | Reverse |
|---|---|---|
| TNFSF-2 | CGAAGGCTCCAAAGAAGACAGT | CAGGGCAATGATCCCAAAGT |
| TNFSF-3 | AGGGTGTACGTCAACATCAGTCA | CACGGCCCCAAAGAAGGT |
| TNFSF-4 | GCCCCTCTTCCAACTGAAGAA | GGTATTGTCAGTGGTCACATTCAAG |
| TNFSF-5 | CCACAGTTCCGCCAAACCT | CACCTGGTTGCAATTCAAATACTC |
| TNFSF-6 | TGGCAGCATCTTCACTTCTA AATG | GAAATGAGTCCCCAAAACAT CTCT |
| TNFSF-7 | CACACTCTGCACCAACCTCACT | TGCACTCCAAAGAAGGTCTCATC |
| TNFSF-8 | ACCACCATATCAGTCAATGTGGAT | GAAGATGGACAACACATTCTCAAGA |
| TNFSF-9 | AGCTACAAAGAGGACACGAAGGA | CGCAGCTCTAGTTGAAAGAAGACA |
| TNFSF-10 | GGGAATATTTGAGCTTAAGGAAAATG | AAAAGGCCCCGAAAAAACTG |
| TNFSF-12 | TACTGTCAGGTGCACTTTGATGAG | CGCAGTGGCTGAGAATTCCT |
| TNFSF-13 | ATATGGTGTCCGAATCCAGGAT | CCTGACCCATGGTGAAAGTCA |
| TNFSF-13B | ATGCCTGAAACACTACCCAATAATT | GCAAGTTGGAGTTCATCTCCTTCT |
| TNFSF-14 | CGTCCGTGTGCTGGATGA | CATGAAAGCCCCGAAGTAAGAC |
| TNFSF-15 | TGCGAAGTAGGTAGCAACTGGTT | CCATTAGCTTGTCCCCTTCTTG |
| TNFSF-18 | CGGCTGTATAAAAACAAAGACATGAT | TCCCCAACATGCAATTCATAAG |
| RNA34 | AGCCCCCTCACTCCCAAA | GGGTGCTGTGCTTCTGTGAAC |

Figure 2:
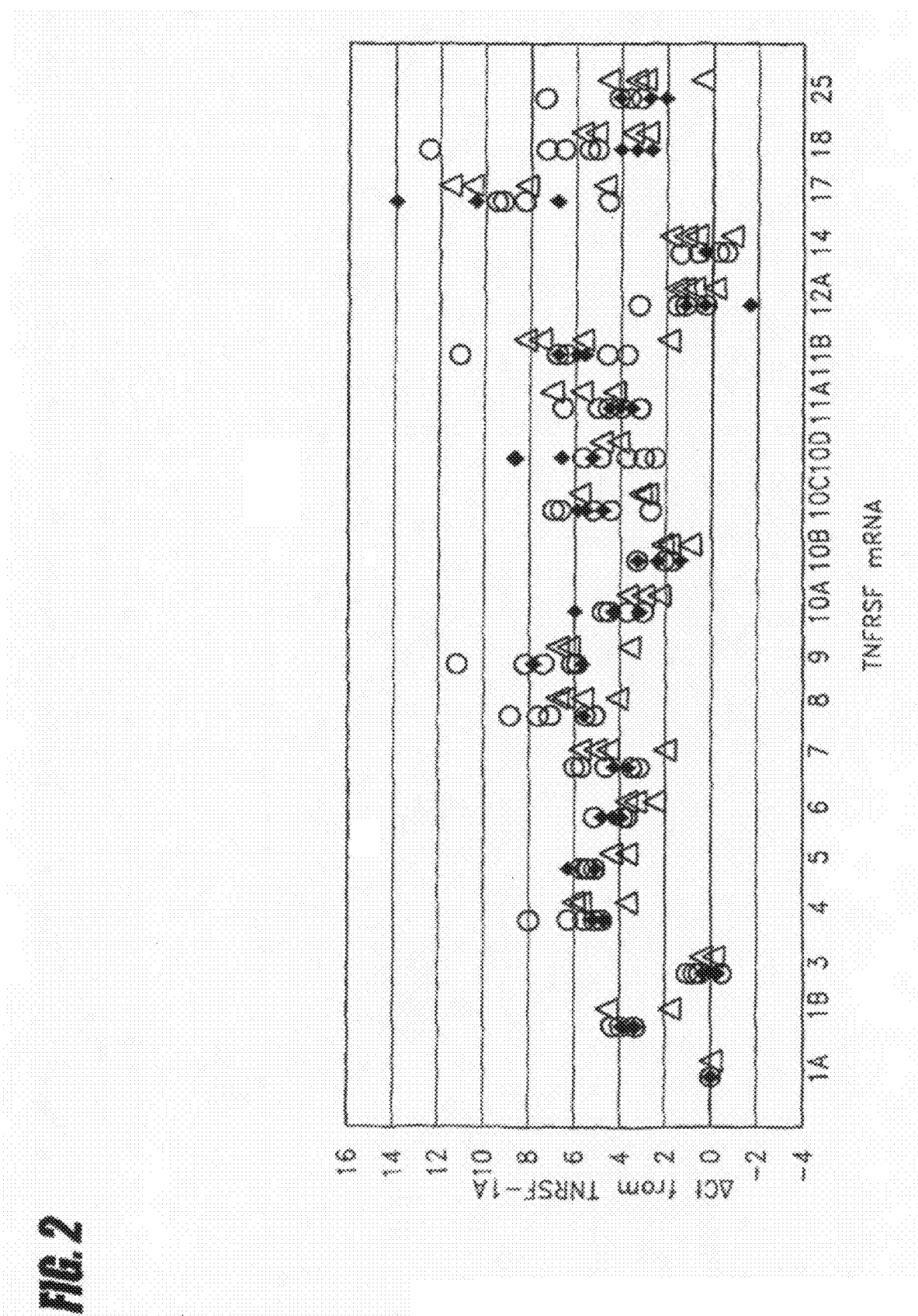
FIG. 2 shows the results of an analysis of TNF-R superfamily mRNAs expressed in tissue samples taken from various adenocarcinomas and squamous cell carcinomas.

The quantity of each mRNA was determined by the method described above as modified below. In brief, approximately 125 mg of frozen cancer specimens were mixed with 1 mL lysis buffer supplemented with 1% 2-mercaptoethanol (Bio Rad), 0.5 mg/mL proteinase Et (Pierce), 0.1 mg/mL salmon sperm DNA (5 Prime Eppendorf/Brinkmann), 0.1 mg/mL *E. coli* tRNA (Sigma), 10 mM each of specific reverse TNF-R superfamily subtype primers, and 11 molecules/mL of synthetic RNA34 as an external control, and homogenized by Polytron (Brinkmann). Seventy μL of these lysates were applied to oligo(dT)-immobilized microplate (GenePlate, RNAture) for mRNA purification. Following overnight incubation at 4° C., the microplates were washed with 100 μL plain lysis buffer 3 times, and then with 150 μL wash buffer (0.5 mol/L NaCl, 10 mmol/L Tris, pH 7.4, 1 mmol/L EDTA) 3 times at 4° C. The cDNA was directly synthesized in each well by adding 30 μL buffer containing 1× RT-buffer (50 mmol/L KCl, 10 mmol/L Tris-HCl, pH 8.3, 5.5 mmol/L MgCl$_2$, no dithiothreitol), 1.25 mmol/L each of dNTP, 4 units rRNasin, and 80 units of MMLV reverse transcriptase (Promega) (without primers), and incubation at 37° C. for 2 hours. 100 μL of water was added to these 30 μL of cDNA, and 4 μL cDNA were transferred to 384-well PCR plates, to which 5 μL iTaq SYBR master mix (BioRad) and 1 μL primer cocktail (10 μmol/L each of forward and reverse primer) were applied, and PCR was conducted in a PRISM 7900HT (Applied Biosystems), with one cycle of 95° C. for 10 min followed by 45 cycles of 95° C. for 30 sec, and 60° C. for 1 min. Each gene was amplified in separate wells. The cycle threshold (Ct), which was the cycle of PCR to generate certain amounts of PCR products (fluorescence), was determined using analytical software (SDS, Applied Biosystems). No amplification was confirmed without cDNA (no primer dimers), and a single peak was detected at melting curve analysis. In order to compare multiple samples among 20 different mRNAs, each Ct was subtracted by the Ct of TNFRSF1A from the same sample (ΔCt, Y-axis). The positive Ct means lower expression than TNFRSF1A, and 1 ΔCt means one half of expression. Each symbol represents the mean value from single specimen. The left-hand side (○♦) of each column in FIG. 2 shows the results from samples of adenocarcinoma including colon, liver, stomach, uterus, and 3 cases of breast cancer (♦), and melanoma. The right-hand side (Δ) shows the results from squamous cell carcinoma, including lung, pharynx, tongue and cervical cancer samples.

Figure 3:
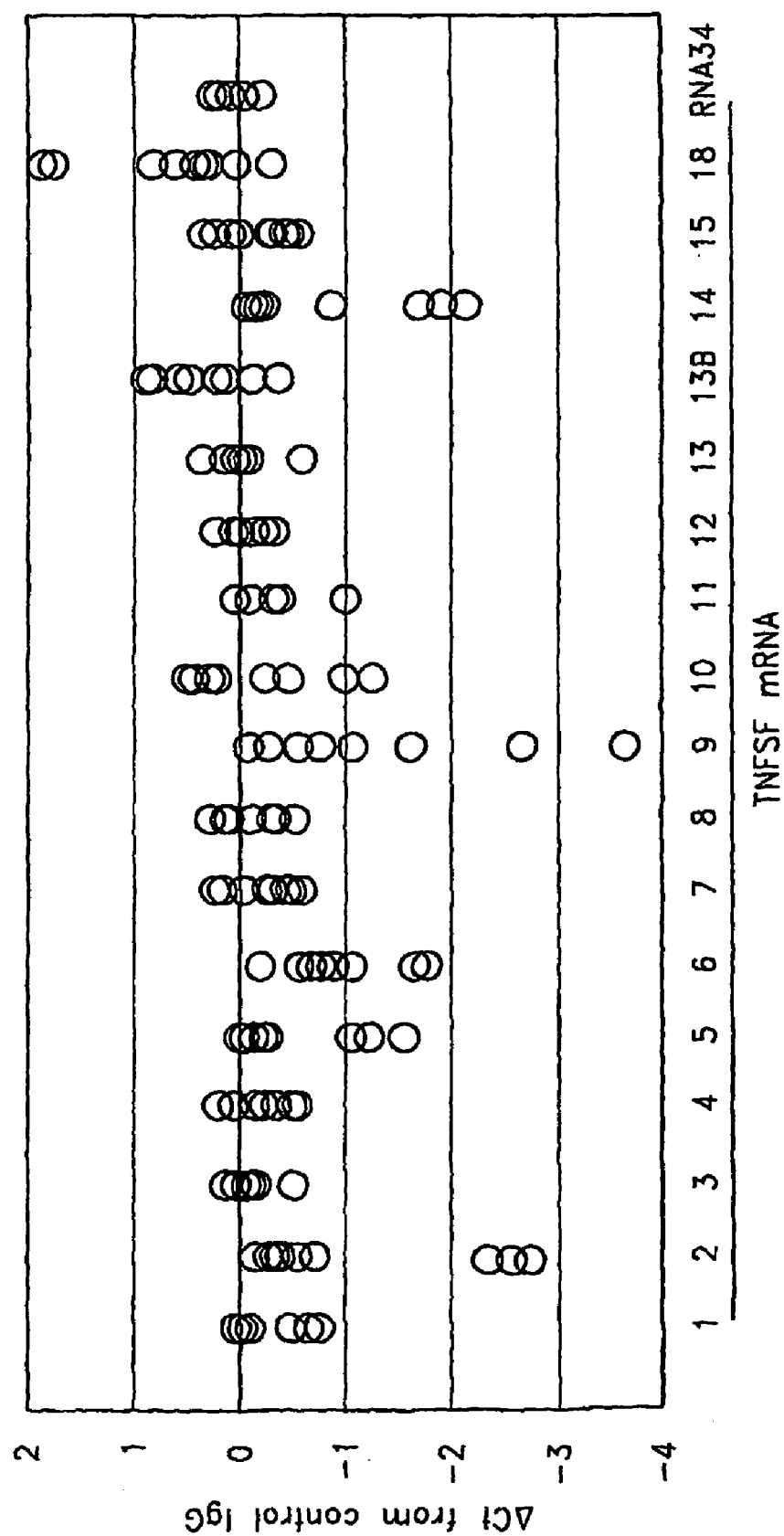
FIG. 3 shows the results of an analysis of TNF superfamily mRNAs induced in peripheral blood leukocytes after exposure of whole blood to anti-human T-cell receptor (TCR) monoclonal antibody.

As for the analysis of the induction of TNF superfamily mRNA in heparinized whole blood by anti-human T cell receptor (TCR) monoclonal antibody, the results of which are shown in FIG. 3, sixty 1 μL of whole blood was stimulated at 37° C. for only 2 hours in triplicate with 5 μg/mL anti-TCRα/β or control IgG. Fifty μL of blood samples were applied to filterplate to trap leukocytes followed by lysis in the membranes by adding lysis buffer, as described above. The purification of poly(A)$^+$ mRNA, cDNA synthesis, and real time PCR were conducted as described above. The ΔCt was calculated by subtracting the Ct values of control IgG from the Ct of anti-TCRα/β. Each symbol represents the mean ΔCt from triplicate blood aliquots of single individual. Synthetic RNA34 spiked into the lysis buffer was also quantitated to validate each assay as an external control.

The cycle threshold (Ct), which was the cycle of PCR to generate certain amounts of PCR products (fluorescence), was determined using analytical software (SDS, Applied Biosystems). Although DNA chip technology (see Schena et al, *Quantitative monitoring of gene expression patterns with a complementary DNA microarray*, Science 1995; 270:467-70)

is capable of analyzing many genes simultaneously, it lacks the capability of exact quantitation, and generally requires more than 3 folds increases as meaningful results. In contrast, the DNA quantitation technology described above provides more accurate quantitation by considering mRNA recovery and cDNA synthesis efficiency in each sample, and as small as 150% (1.5-fold) changes can be detected with statistical significance. Thus, each mRNA was analyzed by SYBR Green real time PCR (see Morrison et al., *Quantification of low-copy transcripts by continuous SYBR Green I monitoring during amplification*, Biotechniques 1998 June; 24(6):954-8, 960, 962) individually from each cDNA prepared by this method, as described above.

FIG. 2 shows the results of TNF-R superfamily mRNA expression in various cancers (colon, breast, liver, stomach, uterus, melanoma, lung, pharynx, tongue, and cervix). In order to compare multiple samples among 20 different mRNAs, the Ct of TNF-R superfamily subtype 1A from the same sample was subtracted from each observed Ct ($\Delta$Ct, Y-axis). A positive Ct value means a lower level of expression than TNFR superfamily subtype 1A, and 1 $\Delta$Ct means one-half the level of expression. As shown in FIG. 2, almost all cancer tissues expressed high levels of TNF-R superfamily subtypes 1A, 3, 12A, and 14. This indicates that if cancer-infiltrating leukocytes are capable of producing TNF superfamily subtype 1 (i.e., lymphotoxin) (corresponding to TNF-R superfamily subtype 3), TNF superfamily subtype 2 (i.e., TNF$\alpha$) (corresponding to TNF-R superfamily subtypes 1A and 1B), TNF superfamily subtype 12 (corresponding to TNF-R superfamily subtype 12A), TNF superfamily subtype 14 (corresponding to TNF-R superfamily subtype 14) or a combination of these ligands at infiltrating sites, any of these types of cancers may be eradicated. Although the expression levels of TNF-R superfamily subtypes 4, 5, 8, 9, 11A and 11B, and 17 were very low in the assessed samples (FIG. 2), the possibility that other samples may express these receptor subtypes cannot be ruled out. Accordingly, the inducibility of TNF superfamily subtype 4 (corresponding to TNF-R superfamily subtype 4), TNF superfamily subtype 5 (i.e., CD40 ligand) (corresponding to TNF-R superfamily subtype 5), TNF superfamily subtype 8 (i.e., CD30 ligand) (for TNF-R superfamily subtype 8), and TNF superfamily subtypes 13 and 13B (corresponding to TNF-R superfamily subtype 17) in leukocytes may also be important for cancer immunotherapy. Although huge individual-to-individual variation exists, the inducibility in leukocytes of TNF superfamily subtype 6 (i.e., Fas ligand) (for TNF-R superfamily subtype 6), TNF superfamily subtype 7 (i.e., CD27 ligand) (for TNF-R superfamily subtype 7), TNF superfamily subtype 11 (for TNF-R superfamily subtypes 11A and 11B), TNF superfamily subtype 18 (for TNF-R superfamily subtype 18), and TNF superfamily subtype 15 (i.e., ligand of DR3) (for TNF-R superfamily subtype 25) may be important for cancers in which expression levels of the corresponding receptors are high. Although TNF-R superfamily subtype 10A mRNA exhibited high expression in cancers, the mRNA expression of decoy receptor TNF-R superfamily subtype 10B (see Sheridan et al., *Control of TRAIL-induced apoptosis by a family of signaling and decoy receptors*, Science 1997 Aug. 8; 277(5327):818-21 and Pan et al., *An antagonist decoy receptor and a death domain-containing receptor for TRAIL*, Science 1997 Aug. 8; 277(5327):815-8) was higher than TNF-R superfamily subtype 10A. Nevertheless, TNF-R superfamily subtype 10 (i.e., TRAIL) may still be a useful target for therapy of some cancers. There is no major difference between adenocarcinoma/melanoma (shown on the left-hand side of each column in FIG. 2) and squamous cell carcinoma (shown on the right-hand side of each column in the Figure).

The T-cell receptor (TCR) is the cell surface molecule of cytotoxic T cells that recognizes specific foreign non-self molecules. The TCR's role in the initial steps of antigen presentation, as well as cancer killing, is well known (see, e.g., Mami-Chouaib, *Antitumor cytotoxic T-lymphocyte response in human lung carcinoma: identification of a tumor-associated antigen*, Immunol Rev. 2002 October; 188:114-21). Although typical experiments in cellular immunology employ pure systems using isolated cells suspended in an artificial solution, the mRNA assay employed in the present embodiments permits the identification of changes in various mRNA levels after ex vivo stimulation of whole blood. Because the latter is more physiological than the former pure system, the present embodiments employ a simulation of TCR-target molecule interactions in whole blood, where cell-to-cell and cell-to-plasma interactions exist.

Since whole blood contains not only cytotoxic T cells, but also other types of leukocytes, the TCR was stimulated specifically by anti-human $\alpha/\beta$ TCR mouse monoclonal IgG1 k ("anti-TCR," obtainable from BioLegend). As a control, the same concentrations of purified mouse IgG1 k (also obtainable from BioLegend) were also used. 60 $\mu$L of whole blood was stimulated at 37° C. for only 2 hours in triplicate with 5 $\mu$g/mL anti-TCR or control IgG. The dose and incubation time were determined by preliminary analysis of the effect of anti-TCR antibody on TNFSF mRNA expression in peripheral blood leukocytes, the results of which are shown in FIGS. 4A and 4B. With respect to dose response and kinetics, as shown in FIG. 4A, triplicate aliquots of 60 $\mu$L each of heparinized whole blood was mixed with PBS (○), 10 (■) or 1 (♦) $\mu$g/mL mouse anti-human $\alpha/\beta$ TCR IgG1k, or 10 ( ) or 1 (◇) $\mu$g/mL purified mouse IgG1k, and incubated at 37° C. for 0-7 hours. Then TNFSF-2 mRNA was quantitated as described above. With respect to kinetics, as shown in FIG. 4B, the $\Delta$Ct of TNFSF-2 (•), TNFSF-5 (◇), TNFSF-6 (Δ), TNFSF-9 ( ), and TNFSF-14 (▲) were calculated by subtracting the Ct values of control IgG therefrom. Each data was the mean±standard deviation from triplicate aliquots of whole blood. The $\Delta$Ct was calculated by subtracting the Ct values obtained using control IgG from the Ct values obtained using anti-TCR.

As shown in FIG. 3, anti-TCR stimulation specifically induced TNF superfamily subtypes 2, 5, 6, 9, 10, and 14. The results of TNF superfamily subtypes 2 and 14 are particularly interesting, because the mRNA expression levels of these receptors were high in all types of cancers (see FIG. 2). Simultaneous activation of multiple TNF/TNF-R superfamily subtype-related cascades may prevent resistance mechanisms of cancer cells, similarly to combination chemotherapy. The results obtained with control synthetic RNA34 spiked into the lysis buffer showed very small changes, less than ±0.3 $\Delta$Ct (RNA34 in FIG. 3), suggesting that the assay system is reliable. More importantly, the TCR responses exhibited substantial individual-to-individual variation, and 6 out of 9 (66%) and 5 out of 9 (56%) individuals failed to show anti-TCR-mediated induction of TNF superfamily subtypes 2 and 14, respectively. Furthermore, the individuals who showed negative TNF superfamily subtype 2 responses also showed negative TNF superfamily subtype 14 responses. However, these individuals did show other positive TNF superfamily ligands.

Embodiment 3

In this embodiment, as in Embodiment 1, heat-aggregated human IgG (HAG), which is used widely as a model of the immune complex as found in ADCC, was used to stimulate the Fc receptors of leukocytes in whole blood. In brief, human IgG (Sigma) was suspended in PBS at 20 mg/mL and heated at 63° C. for 20 min. Sixty µL of whole blood was stimulated at 37° C. for only 2-4 hours in triplicate with 200 µg/mL HAG or control phosphate-buffered saline (PBS). The dose of HAG and incubation time were determined by preliminary analysis, as shown in FIGS. 5 and 6.

FIG. 5A shows the results of an analysis of the dose response. Triplicate aliquots of 60 µL each of heparinized whole blood were mixed with various concentrations of human IgG (○), or HAG (•) and incubated at 37° C. for 2 hours. FIG. 5B shows the results of an analysis of kinetics. Triplicate aliquots of 60 µL each of heparinized whole blood was mixed with PBS (○), or 200 mg/mL HAG (•) and incubated at 37° C. for 0-12 hours. TNFSF-15 mRNA was then quantitated. Each data was the mean±standard deviation from triplicate aliquots of whole blood.

Figure 6:
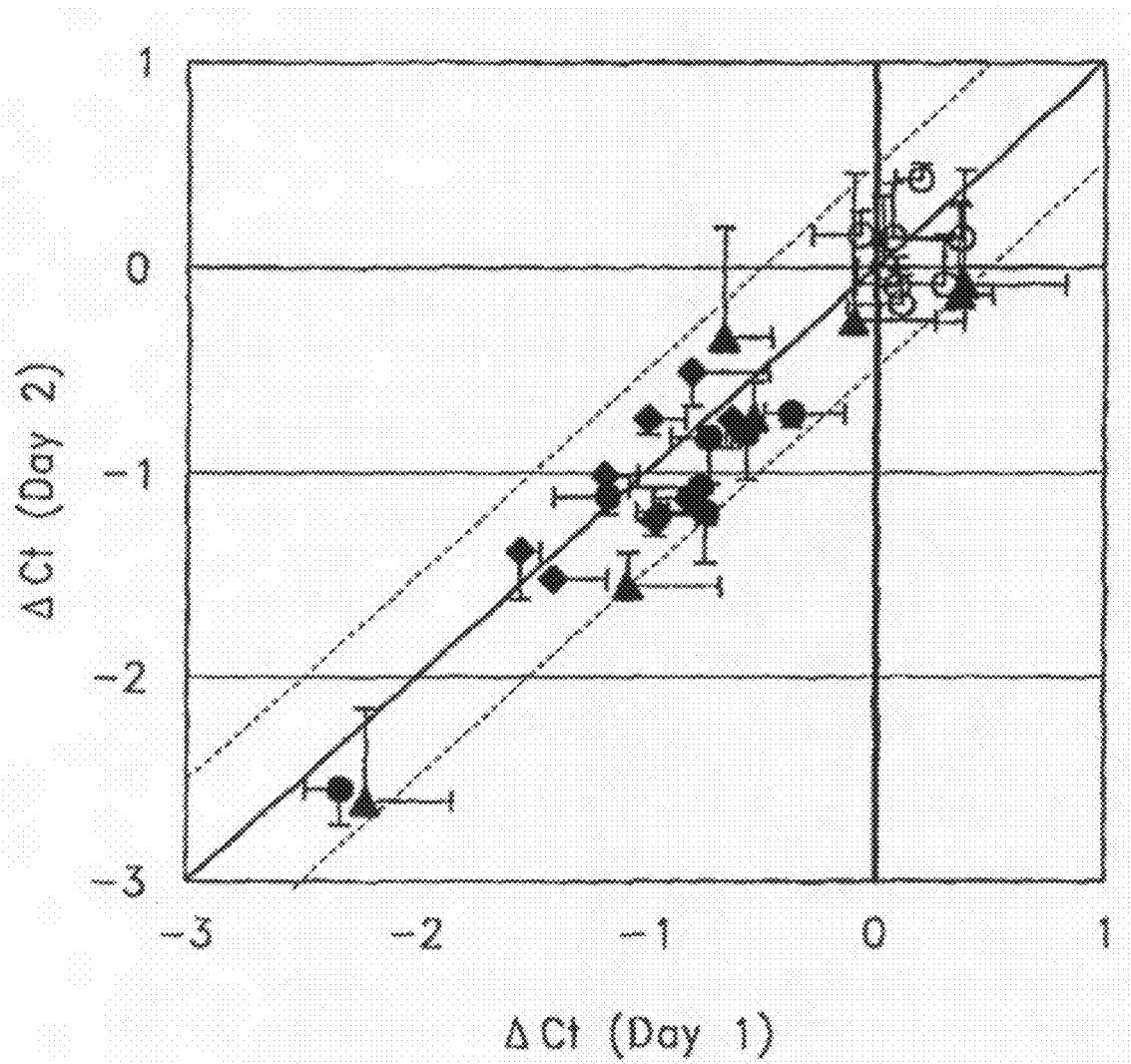
FIG. 6 shows the results of a repetition of the analysis of FIG. 5 with respect to several TNF superfamily subtype mRNAs and control mRNA.

FIG. 6 shows the results of an analysis of reproducibility. Blood was drawn from the same individuals within 1-3 days, and HAG-induced TNFSF mRNA and control RNA34 was quantitated. The symbols indicate ○: RNA34, •: TNFSF-2, ◆: TNFSF-8, and ▲: TNFSF-15, respectively. Each data was the mean±standard deviation from triplicate aliquots of whole blood. The solid line is the line where two data are identical. The dotted lines indicate ±0.5 ΔCt.

Figure 7:
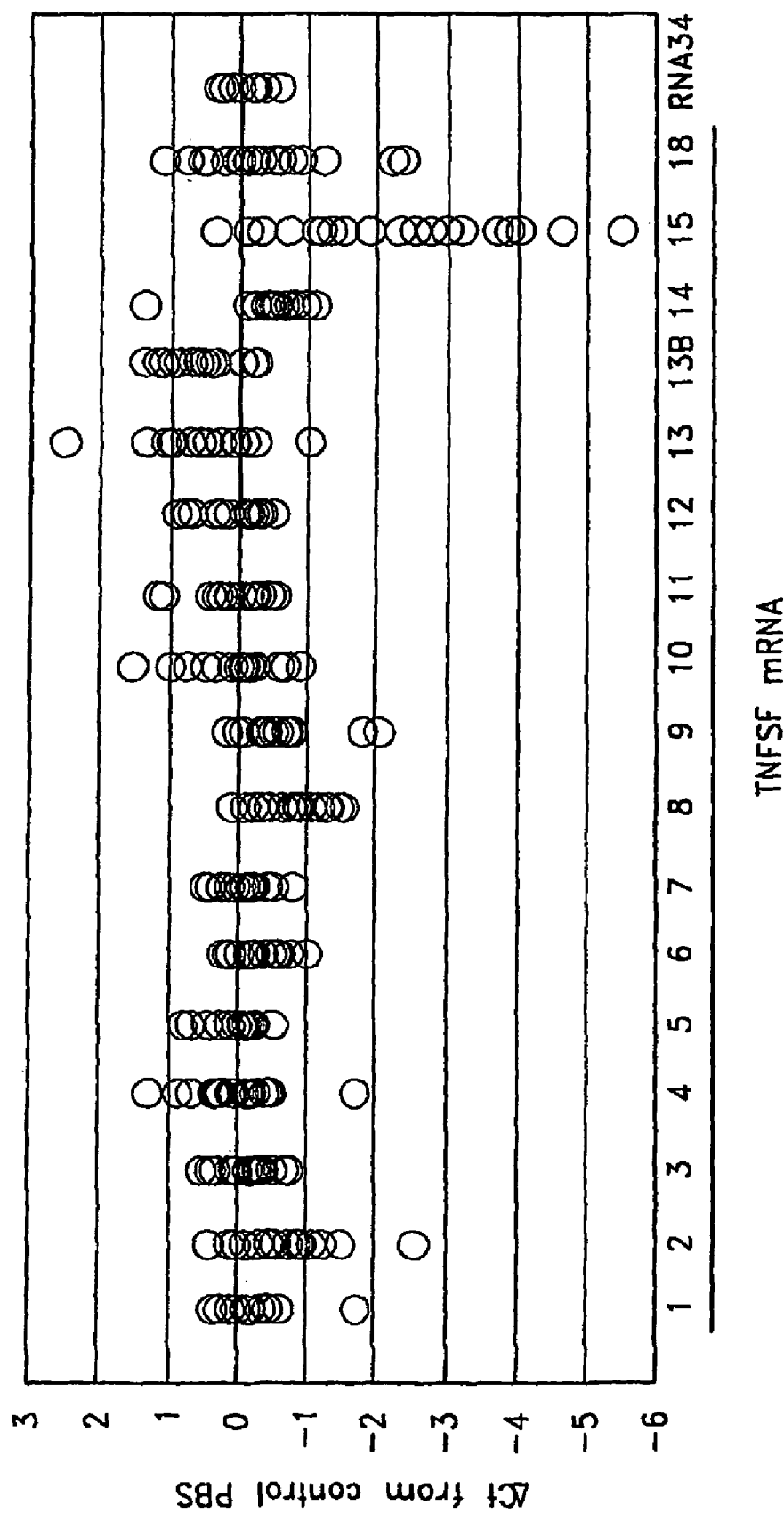
FIG. 7 shows the results of an analysis of TNF superfamily mRNAs induced in peripheral blood leukocytes after exposure of whole blood to HAG.

As shown in FIG. 7, HAG mainly induced expression of TNF superfamily subtypes 2, 8, 14, 15, and 18. The induction of TNF superfamily subtype 15 was higher than that of the TNF superfamily subtypes obtained with anti-TCR stimulation (FIG. 3). Moreover, HAG responses exhibited substantial individual-to-individual variation. Some individuals expressed TNF superfamily subtype 15 alone, and others expressed TNF superfamily subtypes 2 and 8 without TNF superfamily subtype 15 responses. Interestingly, all individuals showed at least 1 TNF superfamily response. The results of control RNA34 spiked into the lysis buffer showed very small changes of less than ±0.6 ΔCt (RNA34 in FIG. 3), suggesting that the assay system is reliable. In order to test the reproducibility of the assay, blood was drawn from the same individuals twice within 1-3 days. However, the results were very similar, with ΔCt differences of less than 0.5 (FIG. 6). Among nine individuals whose blood was tested independently using HAG and anti-TCR stimulation, the TNF superfamily subtype 15 expression response induced by HAG stimulation did not correlate with the TNF superfamily subtypes 2 and 14 expression response induced by anti-TCR stimulation.

Embodiment 4

In this embodiment, whole blood from several individuals was subjected to HAG stimulation, and the changes in the mRNA levels of a group of chemokines were assessed in the same manner as described in Embodiment 1. RNA34 and CD4 mRNA were employed as controls. The forward and reverse primer sequences for the assayed chemokine mRNAs are shown in FIG. 8.

Figure 9:
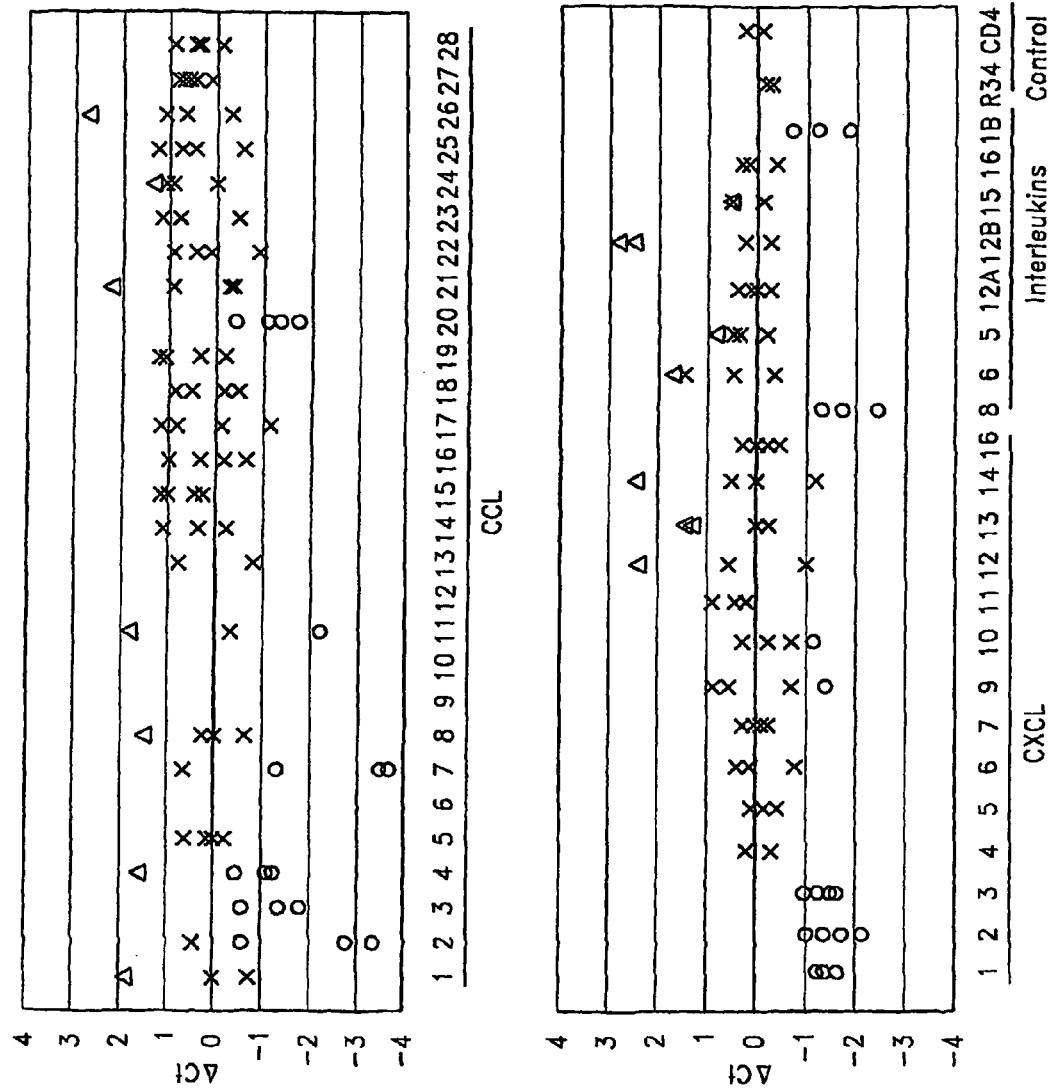
FIG. 9 shows the results of an analysis of chemokine mRNAs induced in peripheral blood leukocytes after exposure of whole blood to HAG.

The results of the analysis are shown in FIG. 9. In the Figure, the circles indicate individuals in which the particular chemokine mRNA level was significantly induced by HAG stimulation. Triangles indicate a significant reduction in the mRNA level after stimulus, while X symbols indicate no significant change. As can be seen from FIG. 9, the responses were varied among individuals, although there were points of commonality: for example, all of the tested individuals showed significant induction of CCL-3 and -20; CXCL-1, -2, and -3; and IL-8 and -1B.

These results indicate that it will be possible to identify the likelihood that a cancer patient will be able to recruit more leukocytes to the diseased area, and if a connection is established between specific chemokines and specific leukocyte populations, data such as that shown in FIG. 9 could be used to assess the likelihood of recruiting leukocyte populations capable of effectively combating the tumor, based on TNF/TNF-R matching analysis between the leukocyte population recruited and the tumor cells.

Embodiment 5

In this embodiment, the effects of various dietary components such as supplements on the HAG-induced changes in TNF superfamily subtype 3 mRNA levels were assessed. "Dietary components" refers to any compound or substance that may be ingested by a mammal, while "dietary supplements" indicates those beneficial dietary components, such as vitamins and natural extracts, that are used to supplement the diet of mammals, as well as other chemical compounds such as pharmaceuticals. As such, "dietary component" is broader and subsumes "dietary supplements" within it. The dietary components employed were: vitamin A (10 nM, final concentration), genistein (soy) (100 nM), curcumin (spice turmeric) (100 nM), and quercetin (plant pigments flavonoids) (100 nM). All of these dietary components have reported effects on the immune system or cancer or both. Vitamin A is known to stimulate the immune system. Genistein has been found in some studies to have anticarcinogenic activity; possible mechanisms of action include upregulation of apoptosis, inhibition of angiogenesis, inhibition of DNA topoisomerase II and inhibition of protein tyrosine kinases. Curcumin has proapoptotic effects in neoplastic cells and interferes with the activity of the transcription factor NF-κB, which is often highly overexpressed in such cells. Quercetin has been shown to boost natural killer cell activity in rats and to inhibit degranulation of mast cells, basophils and neutrophils. In this embodiment, phosphate-buffered saline was employed as a control.

Heparinized whole blood was pre-incubated with various dietary supplements at 37° C. for 1 hour (at the blood concentrations described above), then stimulated with 1.2 µL of heat-aggregated IgG for four hours. The blood was then incubated at 37° C. for 2 hours. The level of TNF superfamily subtype 3 mRNA was then assessed using the method described in Embodiment 1. The primer sequences are given in Table 2 above. TNF superfamily subtype 3 is also known as lymphotoxin-alpha (LT alpha), tumor necrosis factor-beta (TNF-beta), and lymphotoxin-beta (LT beta). Secreted LT alpha assembles as a soluble homotrimer, LT alpha 3. Secreted LT alpha also complexes with the membrane-associated LT beta to generate two types of heterotrimers, LT alpha 1/beta and LT alpha 2/beta 1. Subtype 3 is expressed by activated naive CD4 cells, unpolarized IL-2-secreting effectors, and Th1 effectors, and subtype 3-specific receptors are expressed by some tumor cells.

Figure 10:
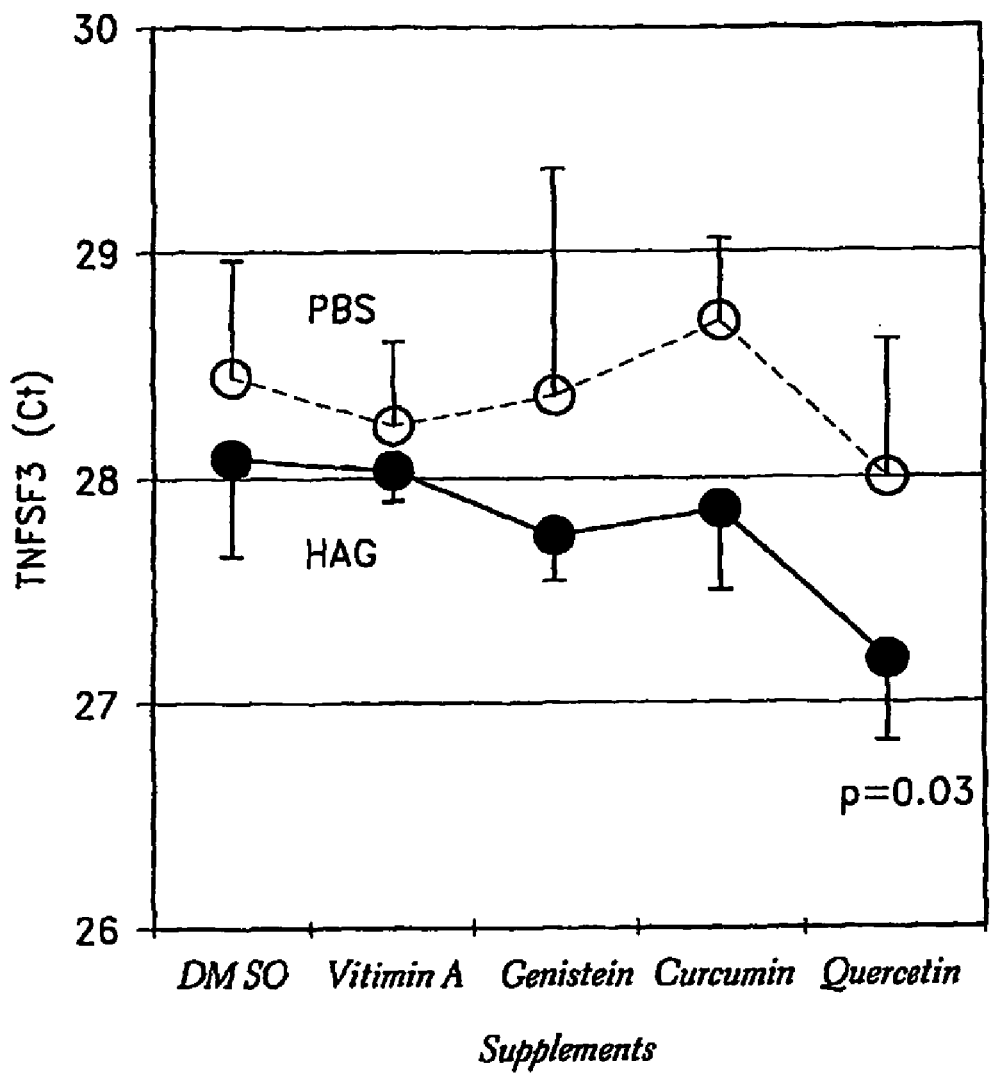
FIG. 10 shows the results of an analysis of TNF superfamily subtype 3 mRNA induced in peripheral blood leukocytes after exposure to HAG of whole blood aliquots previously stimulated with either a dietary supplement or a control stimulus.

The results are shown in FIG. 10. In FIG. 10, the open circles indicate TNF superfamily subtype 3 values obtained using a PBS control, while closed circles indicate subtype 3 values obtained when using the HAG stimulus. Basal levels of subtype 3 mRNA were unchanged by pretreatment with dietary supplements (open circles). However, the results indicate that HAG caused a significant (p=0.03) induction of TNF superfamily subtype 3 expression in blood exposed to quercetin. If this individual also had tumor cells expressing the appropriate TNF-R subtype (subtype 3), an increase in the expression of this gene may increase apoptosis of the tumor cells, so that quercetin would be a good candidate for inclusion in a diet having anti-cancer properties for this individual. The Y-axis values in FIG. 10 show the cycle threshold (Ct). Each symbol is the mean±S.D. from triplicate aliquots of 50 mL heparinized whole blood.

One of skill in the art will appreciate that it would also be possible to screen pharmaceuticals and other chemical compounds for similar effects on the expression of particular TNF superfamily subtypes or chemokines, so that the system of the present embodiment may be broadly employed to screen for substances useful in mounting an immune response to cancer in a particular individual.

Cancer infiltrating leukocytes are often observed in surgically removed tissue specimens by pathological examinations. However, these findings are not always an unambiguous good sign for patients: cancer progressions sometimes occur even when leukocyte infiltration exists. Pathologists are often puzzled when this occurs. The present embodiments provide a further refinement of this technique: matching TNF-R superfamily subtypes in cancer cells and TNF superfamily subtypes in infiltrating leukocytes may be a good prognostic sign, particularly when chemokine induction is also demonstrated. Pathological analyses of infiltrating leukocytes are difficult to interpret, because we do not know whether each leukocyte encounters cancer cells and whether the TNF superfamily cascade is activated or not. Quantitated base line TNF superfamily mRNA levels are also difficult to interpret. Instead, the embodiments of the present invention employ an analysis of functional changes in the expression of TNF superfamily mRNA subtypes after anti-TCR or HAG stimulation. Since infiltrating leukocytes come from the blood stream, the ex vivo functional assays of the present embodiments will be useful tools for the analysis of immune functions not only in cancer patients, but also in patients suffering from other diseases such as autoimmune diseases, inflammation, transplantation, etc., in terms of diagnostics, therapeutic monitoring, prognostic markers, and identification of effective immunomodulatory drugs, monoclonal antibody-based medicines, gene therapies and vaccines. The assay is simple and physiological (2-4 hours incubation of whole blood without isolation of leukocytes), accurate with meaningful statistical analysis (triplicate aliquots of whole blood as starting materials), and sensitive (60 µL whole blood is enough for all 17 TNF superfamily subtype mRNA quantizations). Due to an extremely small variation in the mRNA data among triplicate aliquots of whole blood, the assay permits the identification of significant changes in gene expression as small as 0.5-1.0 ΔCt in many cases, which is far better than DNA chip-based methodologies or conventional real time PCR. The number of NK cells or cytotoxic T-cells can be quantitated by flow cytometric analysis or immunohistochemical staining, where each cell population is identified by specific cell surface markers. However, it is unclear whether these marker-positive cells really have the expected function at the time of the analysis. Although the method of the present embodiments does not identify a specific cell population with the stimulation responses of each TNF superfamily subtype mRNA, it shows the function as a whole, which is useful for the understanding of individual people. The wide individual variations obtained may lead to the discovery of the specific genetic makeup of individuals. Although the TNF superfamily response showed good reproducibility within 1-3 days (FIG. 6), it can also changes over a long period of time as well as by administration of dietary supplements and exercise, suggesting the involvement of non-genetic factors. Thus, the methods of the present embodiments represent an advance toward future individualized cancer immunotherapies.

Such individualized cancer immunotherapies will be based on increasing the expression of the appropriate TNF superfamily subtypes in blood leukocytes, as well as recruiting subtype-specific leukocytes via appropriate chemokine signaling. The system and method of the embodiments described above will be useful in drug screening, validation, and clinical trials. Moreover, the same system can be applicable to autoimmune diseases, where inhibition of appropriate TNF superfamily will be the drug target.

An abundant supply of appropriately equipped police officers in the city is only meaningful when they are dispatched to the crime scene. If an officer encounters a group of criminals, his or her primary job is to call help to bring more colleagues to the scene rather than to try to arrest them alone. For cytotoxic T-cells, this action may correspond to the release of chemotactic factors, such as CCL and CXCL chemokines, and interleukins (ILs) (sequences are available from GenBank and UniGene). Thus, monitoring HAG inducibility of CCLs, CXCLs, and in peripheral blood leukocyte is also important. Like a police dispatcher, an oncologist may be able to orchestrate each patient's own immune cells by monitoring their supply in peripheral blood.

What is claimed is:

1. A method of determining the likely severity of prognosis for a neoplastic disease in a mammal, comprising:
    determining a level of expression of a plurality of tumor necrosis factor (TNF) superfamily subtypes in a first sample of whole blood from the mammal, said mammal having a solid neoplasm;
    exposing a second sample of whole blood of the mammal to a stimulus that activates leukocytes in the whole blood;
    determining a level of expression of the plurality of tumor necrosis factor (TNF) superfamily subtypes in the second sample;
    identifying subtypes that exhibit a statistically significant (p<0.05) change in expression level in said whole blood between said first and second samples,
    identifying TNF-R superfamily subtypes expressed in the solid neoplasm of the mammal; and
    determining a likely lesser severity of prognosis when the identified subtypes of TNF superfamily correspond to specific tumor necrosis factor receptor (TNF-R) superfamily subtypes expressed in said neoplasm of the mammal.

2. The method of claim 1, wherein TNF-R superfamily subtypes expressed in the solid neoplasm are selected from the group consisting of TNF-R superfamily subtypes 1A, 3, 12A, and 14.

3. The method of claim 1, wherein TNF-R superfamily subtypes expressed in the solid neoplasm are identified by a method selected from the group consisting of immunostaining, in situ hybridization, in situ polymerase chain reaction, and in vitro polymerase chain reaction.

4. The method of claim 1, wherein exposing whole blood includes addition of heparin.

5. The method of claim 1, wherein the stimulus is selected from the group consisting of heat-aggregated human IgG and anti-human α/β T-cell receptor monoclonal IgG.

6. The method of claim 1, wherein the tumor necrosis factor receptor superfamily subtypes expressed by the solid neoplasm cells are selected from the group consisting of TNF-R superfamily subtypes 1A, 1B, 3, 4, 5, 6, 7, 8, 9, 10A, 10B, 10C, 10D, 11A, 11B, 12A, 14, 17, 18, and 25.

7. The method of claim 1, wherein the tumor necrosis factor superfamily subtypes expressed in said exposed whole blood are mRNA subtypes selected from the group consisting of TNF superfamily subtypes 1, 2, 3, 4, 5, 6, 7, 8, 9, 10, 11, 12, 13, 13B, 14, 15, and 18.

8. A method of determining the likely severity of prognosis for a neoplastic disease in a mammal according to claim 1, further comprising:
 determining a level of expression of a plurality of chemokines in a first sample of whole blood from the mammal;
 exposing a second sample of whole blood of the mammal to a stimulus that activates leukocytes in the whole blood;
 determining a level of expression of the plurality of chemokines in the second sample;
 determining a likely lesser severity of prognosis when chemokines that exhibit a statistically significant (p<0.05) change in expression level in said whole blood between said first and second samples are identified.

9. The method of claim 8, wherein said chemokines are selected from the group consisting of CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL9, CXCL10, CXCL11, CXCL12, CXCL13, CXCL14, CXCL16, IL1B, IL5, IL6, IL8, IL12A, IL12B, IL15, and IL16.

10. A method of determining the likely utility of a dietary component for treating neoplastic disease in a mammal, comprising:
 obtaining a first sample of whole blood of the mammal, said mammal having a solid neoplasm;
 exposing a second sample of whole blood of the mammal to the dietary component;
 exposing the first and second samples of whole blood of the mammal to a stimulus that activates leukocytes in the whole blood;
 determining a level of expression of a plurality of tumor necrosis factor (TNF) superfamily subtypes in the first and second samples of whole blood from the mammal;
 identifying subtypes that exhibit a statistically significant (p<0.05) change in expression level in said whole blood between said first and second samples,
 identifying TNF-R superfamily subtypes expressed in the solid neoplasm of the mammal; and
 determining that the dietary component likely has utility for treating the neoplastic disease when the identified subtypes of TNF superfamily correspond to specific TNF-R superfamily subtypes expressed in said neoplasm of the mammal.

11. The method of claim 10, wherein the first sample is exposed to a control stimulus before the exposure to the stimulus that activates leukocytes in the whole blood.

12. The method of claim 10, wherein TNF-R superfamily subtypes expressed in the solid neoplasm are selected from the group consisting of TNF-R superfamily subtypes 1A, 3, 12A, and 14.

13. The method of claim 10, wherein TNF-R superfamily subtypes expressed in the solid neoplasm are identified by a method selected from the group consisting of immunostaining, in situ hybridization, in situ polymerase chain reaction, and in vitro polymerase chain reaction.

* * * * *

UNITED STATES PATENT AND TRADEMARK OFFICE
CERTIFICATE OF CORRECTION

| | |
|---|---|
| PATENT NO. | : 7,741,023 B2 |
| APPLICATION NO. | : 11/917151 |
| DATED | : June 22, 2010 |
| INVENTOR(S) | : Mitsuhashi |

It is certified that error appears in the above-identified patent and that said Letters Patent is hereby corrected as shown below:

(Fig. 10) at line 6, Change "Vitimin" to --Vitamin--, therefore.

In column 2 at line 61, Change "*GeneBank" to --*GenBank--, therefore.

In column 4 at line 46, Change "1C," to --10C,--, therefore.

In column 6 at line 47-48, Change "150 ΔL" to --150 µL--, therefore.

In column 7 at line 2, Change "150 mL" to --150 µL--, therefore.

In column 7 at line 6, Change "30 mL" to --30 µL--, therefore.

In column 7 at line 12, Change "5 mL" to --5 µL--, therefore.

In column 7 at line 38, Change "60 mL)." to --60 µL).--, therefore.

In column 8 at line 20, Change "amplification." to --amplification,--, therefore.

In column 9-10 at line 11 (Table 2), Change "TTCTGCCCCGTTAACAACAG" to --TTCTGCCCCGTTTAACAACAG--, therefore.

In column 9-10 at line 12 (Table 2), Change "TTGCTGCTCAGAGACGAAAGTC" to --TTGCTGCTCAGAGACGAAAGTG--, therefore.

In column 11 at line 38, Change "Et" to --K--, therefore.

In column 11 at line 41, Change "11" to --$10^7$--, therefore.

In column 12 at line 50, Change "sixty 1 µL" to --sixty µL--, therefore.

Signed and Sealed this
Twenty-ninth Day of March, 2011

David J. Kappos
*Director of the United States Patent and Trademark Office*

In column 19 at line 8, In Claim 6, after "neoplasm" delete "cells", therefore.